US012239657B2

(12) United States Patent
James et al.

(10) Patent No.: US 12,239,657 B2
(45) Date of Patent: Mar. 4, 2025

(54) IRON COMPOSITIONS AND METHODS OF MAKING AND USING THEM

(71) Applicant: American Regent, Inc., Shirley, NY (US)

(72) Inventors: Roshan James, Westerville, OH (US); Bindhu Madhavi Rayaprolu, Columbus, OH (US); Ting Zhang, Westerville, OH (US); Meng Zhong, Westerville, OH (US)

(73) Assignee: Vifor (International) AG, ST. Gallen (CH)

( * ) Notice: Subject to any disclaimer, the term of this patent is extended or adjusted under 35 U.S.C. 154(b) by 0 days.

(21) Appl. No.: 17/895,738

(22) Filed: Aug. 25, 2022

(65) Prior Publication Data

US 2023/0084291 A1 Mar. 16, 2023

Related U.S. Application Data

(60) Provisional application No. 63/237,765, filed on Aug. 27, 2021.

(51) Int. Cl.
| | | |
|---|---|---|
| *A61K 31/7135* | (2006.01) | |
| *A61K 9/00* | (2006.01) | |
| *A61K 47/02* | (2006.01) | |
| *A61K 47/22* | (2006.01) | |

(52) U.S. Cl.
CPC ........ *A61K 31/7135* (2013.01); *A61K 9/0019* (2013.01); *A61K 47/02* (2013.01); *A61K 47/22* (2013.01)

(58) Field of Classification Search
CPC .......................... A61K 31/7135; A61K 9/0019
See application file for complete search history.

(56) References Cited

U.S. PATENT DOCUMENTS

| | | |
|---|---|---|
| 6,960,571 B2 | 11/2005 | Helenek et al. |
| 7,169,359 B2 | 1/2007 | Helenek et al. |
| 7,612,109 B2 | 11/2009 | Geisser et al. |
| 7,674,780 B2 | 3/2010 | Newton et al. |
| 7,754,702 B2 | 7/2010 | Helenek et al. |
| 7,964,568 B2 | 6/2011 | Beck et al. |
| 8,030,480 B2 | 10/2011 | Gharpure et al. |
| 8,053,470 B2 | 11/2011 | Xiao et al. |
| 8,058,076 B2 | 11/2011 | Shah et al. |
| 8,431,549 B2 | 4/2013 | Helenek et al. |
| 8,895,612 B2 | 11/2014 | Helenek et al. |
| 9,376,505 B2 | 6/2016 | Geisser et al. |
| 10,478,450 B2 | 11/2019 | Helenek et al. |
| 10,519,252 B2 | 12/2019 | Geisser et al. |
| 11,123,321 B2 | 9/2021 | Geisser et al. |
| 11,291,645 B2 | 4/2022 | Geisser et al. |
| 11,344,568 B2 | 5/2022 | Helenek et al. |
| 11,364,260 B2 | 6/2022 | Helenek et al. |
| 11,406,656 B2 | 8/2022 | Helenek et al. |
| 11,433,091 B2 | 9/2022 | Helenek et al. |
| 2005/0209187 A1* | 9/2005 | Newton ..................... A61P 7/06 536/123.13 |
| 2008/0167266 A1 | 7/2008 | Justus |
| 2008/0213345 A1 | 9/2008 | Hu et al. |
| 2011/0226658 A1 | 9/2011 | Tata-Venkata et al. |
| 2015/0141630 A1 | 5/2015 | Biswas et al. |
| 2018/0147238 A1 | 5/2018 | Thennati et al. |
| 2019/0263939 A1 | 8/2019 | Geisser et al. |
| 2019/0276563 A1 | 9/2019 | Geisser et al. |
| 2019/0328771 A1 | 10/2019 | Helenek et al. |
| 2021/0046062 A1* | 2/2021 | Wehring ............ A61K 31/4422 |
| 2022/0079984 A1 | 3/2022 | Keyser et al. |

FOREIGN PATENT DOCUMENTS

| | | | |
|---|---|---|---|
| CN | 103340827 B | 12/2014 | |
| CN | 106137953 A | * 11/2016 | ............. A61K 47/12 |
| CN | 107106642 A | * 8/2017 | ............. A61K 38/10 |
| EP | 2227222 B1 | * 6/2014 | ......... A61K 31/4172 |

OTHER PUBLICATIONS

Machine Translation of CN106137953A All Pages by Clarivate Analytics (Year: 2016).*
Machine Translation of CN107106642A All Pages by Clarivate Analytics (Year: 2017).*
Venofer Drug Label. Revised Apr. 2019 (Year: 2019).*
International Searching Authority; Notification of Transmittal of the International Search Report and the Written Opinion of the International Searching Authority, or the Declaration. Dec. 6, 2022.
Danielson, Bo G., et al. Iron Therapy with Special Emphasis on Intravenous Administration. Vifor (International) Inc. 1996.
Zou, Peng, et al. Physiochemical Characterization of Iron Carbohydrate Colloid Drug Products. The AAPS Journal, vol. 19, No. 5, Sep. 2017.
Bo G. Danielson, J Am Soc Nephrol 15: S93-S98, 2004.
Funk et al. Criticality of surface characteristics of intravenous iron-carbohydrate nanoparticle complexes: implications for pharmacokinetics and pharmacodynamics. Int. J. Mol. Sci. 2022, vol. 23, Feb. 15, 2022.
Guidance for Industry: Drug Stability Guidelines (p. 1-48), Dec. 9, 2008.
P. Geisser, M. Baer, and E. Schaub, Arzneim.-Forsch./Drug Res. 42 (II), 12, 1439--1452 (1992).
Highlights of Prescribing Information. Venofer(Iron Sucrose) injection, for intravenous use. American Regent, Inc. Rev. Oct. 2020.
Highlights of Prescribing Information. INFeD (iron dextran injection), for intravenous or intramuscular use. Allergan USA Inc., Madison, New Jersey 07940. Rev. Apr. 2021.
Imferon (Iron Dextran injection) package insert. Fisons Pharmaceuticals, Rochester, New York 14623. Rev. May 1989.

(Continued)

*Primary Examiner* — Kortney L. Klinkel
*Assistant Examiner* — Richard Grant Peckham
(74) *Attorney, Agent, or Firm* — Sorell, Lenna & Schmidt, LLP

(57) ABSTRACT

Injectable iron compositions comprising iron, a carbohydrate, a stabilizing agent and water are provided. These iron compositions can be prepared by mixing iron with a carbohydrate and water to form a mixture and adding a stabilizing agent to the mixture to form the stable injectable iron composition. These compositions can be considered "ready-to-use" and can treat a variety of diseases, disorders, or conditions characterized by iron deficiency or dysfunctional iron metabolism, for example, anemia.

34 Claims, No Drawings

(56) References Cited

OTHER PUBLICATIONS

Dexferrum (Iron Dextran Injection USP) Prescribing information. NDA 40-024/S-022. American Regent, Inc., Shirley, New York 11967. Rev. Aug. 2008.
Highlights of Prescribing Information. Ferrlecit (sodium ferric gluconate complex in sucrose) injection, for intravenous use. Sanofi-Aventis US LLC. Bridgewater, NJ 08807. Mar. 2022.
Highlights of Prescribing Information. Injectafer (ferric carboxymaltose) injection, for intravenous use. American Regent. Shirley, New York 11967. Jan. 2018.
Highlights of Prescribing Information. Feraheme (ferumoxytol) injection, for intravenous use. AMAG Pharmaceuticals, Inc. Waltham, Mass. Feb. 2018.
Highlights of Prescribing Information. Monofer/Monoferric(ferric derisomaltose) injection, for intravenous use. Pharmacosmos Therapeutics Inc. Morristown, New Jersey, Feb. 2022.
Mobarra et al. A Review on Iron Chelators in Treatment of Iron Overload Syndromes, Int J Hematol Oncol Stem Cell Res. Oct. 1, 2016; 10(4): 239-247.

* cited by examiner

IRON COMPOSITIONS AND METHODS OF MAKING AND USING THEM

BACKGROUND

Iron containing compositions have been used to treat iron deficiency anemia caused by iron deficiency or dysfunctional metabolism. Parenterally administering iron without any other modifications is highly toxic. To overcome this problem iron carbohydrate complexes have been developed. A water-soluble iron (III) hydroxide sucrose complex is a frequently and successfully used preparation. Intravenous (IV) iron agents are colloids that contain spheroidal iron-carbohydrate nanoparticles. At the core of each particle is an iron-oxyhydroxide gel. The core is surrounded by a shell of carbohydrate that stabilizes the iron-oxyhydroxide, releases the bioactive iron in a controlled manner, and maintains the resulting particles in colloidal suspension. Intravenous or parenteral iron agents share the same core chemistry but differ from each other by the size of the core and the identity and the density of the surrounding carbohydrate. Differences in core size and carbohydrate chemistry determine pharmacologic and biologic differences, including clearance rate after injection, iron release rate in vitro, early evidence of iron bioactivity in vivo, and maximum tolerated dose and rate of infusion.

Injectable iron compositions are known to be effective in a variety of diseases and conditions including, but not limited to, severe iron deficiency, iron deficiency anemia, problems of intestinal iron absorption, intestinal iron intolerance, cases where regular intake of an oral iron preparation is not guaranteed, iron deficiency where there is no response to oral therapy (e.g., dialysis patients), and situations where iron stores are scarcely or not at all formed but would be important for further therapy (e.g., in combination with erythropoietin).

Currently available parenteral iron compositions approved for use in the U.S. include iron dextran (e.g., InFed®, Dexferrum®), sodium ferric gluconate complex in sucrose (Ferrlecit®), iron sucrose (Venofer®), iron isomaltoside (Monofer®) and non-stoichiometric magnetite (superparamagnetic iron oxide) coated with polyglucose sorbitol carboxymethylether (Feraheme®). Of the parenteral iron compositions currently available, serious and life-threatening reactions occur most frequently with iron dextran. In addition, non-life threatening reactions such as arthralgia, back pain, hypotension, fever, myalgia, pruritus, vertigo, and vomiting also can occur. These reactions, while not life-threatening, often preclude further dosing and therefore iron repletion.

Venofer® (iron sucrose injection, USP) 20 mg/mL is composed of the active pharmaceutical ingredient (API) polynuclear iron (III)-hydroxide in sucrose having a molecular weight of approximately 34,000 to 60,000 Daltons (Da) and a proposed structural formula:

$$[Na_2Fe_5O_8(OH)\cdot 3(H_2O)]_n \cdot m(C_{12}H_{22}O_{11})$$

where n is the degree of iron polymerization and m is the number of sucrose molecules associated with the polymerized iron (III)-hydroxide.

Venofer® is indicated for the treatment of iron deficiency anemia in patients with chronic kidney disease (CKD). The poly-nuclear iron (III)-hydroxide-sucrose structure is dissociated into iron and sucrose following intravenous administration, and the iron is transported as a complex with transferrin to target cells including erythroid precursor cells. The iron in the precursor cells is incorporated into hemoglobin as the cells mature into red blood cells. Venofer® IV infusion solutions are prepared in 0.9% NaCl at concentrations ranging from 1 mg to 2 mg of elemental iron per mL and is physically and chemically stable for 7 days at controlled room temperature (25° C.±2° C.). In addition to Venofer®, other parenteral iron compositions approved in the United States include iron dextran (e.g., InFed®, Dexferrum®), sodium ferric gluconate complex in sucrose (Ferrlecit®), and ferric carboxymaltose injection (Injectafer®), iron isomaltoside (Monofer®) and non-stoichiometric magnetite (superparamagnetic iron oxide) coated with polyglucose sorbitol carboxymethylether (Feraheme®). Those approved in the UK also includes iron sucrose (Sucrofer®, UK Claris).

Some intravenous iron compositions are administered by intravenous infusions. Typically, intravenous infusions use larger volume IV bags or IV bottles containing delivery vehicles, such as normal saline or dextrose, which are connected to a delivery tube set. Intravenous infusions use either gravity or pumps to deliver the medication into the vein over a period of at least 20 minutes to one hour or longer.

Intravenous infusions can be time consuming for healthcare personnel (e.g., nurse, doctor, etc.) and may require additional steps and equipment. For example, the healthcare personnel has to choose the IV bag or bottle (e.g., 50 mL to 250 mL or greater) with the correct volume of a compatible delivery vehicle (e.g., saline) and inject the dosage of the iron composition to dilute it into the delivery vehicle for administration to the patient. If the wrong delivery vehicle is chosen and the medication is incompatible with the chosen delivery vehicle, the medication can be unstable causing unwanted precipitates to form, which is not beneficial to the patient.

Thus, there is a need for ready-to-use (RTU) stable injectable iron compositions for infusion. These stable injectable iron compositions can be administered by intravenous push, which avoids many of the drawbacks associated with slower larger volume intravenous infusions (e.g., 1000 mL or greater). The compositions of this application address these and other needs by providing a pre-mixed, ready-to-use, injectable composition of iron that is stable and provides a suitable elemental iron concentration for immediate use, without the need for dilution.

SUMMARY

Stable injectable iron compositions including iron, a carbohydrate, a stabilizing agent and water are provided. In some embodiments, the injectable iron compositions of the present application are pre-mixed, ready-to-use or ready to administer and stable injectable compositions, which provide suitable elemental iron concentrations for immediate use, without the need for dilution in a larger volume delivery vehicle (e.g., in volumes of 1000 mL or greater).

In some of these iron compositions, the iron comprises, consists essentially of, or consists of elemental iron and the carbohydrate comprises a monosaccharide, a disaccharide, an oligosaccharide (e.g., usually containing two to about ten sugar residues) or a polysaccharide (e.g., usually contain more than ten sugar residues). In various embodiments, (i) the monosaccharide comprises glucose, galactose, fructose or mixtures thereof; (ii) the disaccharide comprises sucrose, lactose, maltose, or mixtures thereof; (iii) the oligosaccharide comprises raffinose, stachyose, verbascose or mixtures thereof; or (iv) the polysaccharides comprise starch, a starch derivative, dextran, cellulose, glycogen or mixtures thereof.

In many embodiments, the elemental iron and the carbohydrate used in these iron compositions form a colloidal iron (III) carbohydrate complex. Useful carbohydrates for these iron compositions include, without limitation, iron carboxymaltose, iron sucrose, iron polyisomaltose, iron polymaltose, iron gluconate, iron sorbitol, iron hydrogenated dextran, iron derisomaltose (e.g., ferric derisomaltose or iron isomaltoside), ferumoxytol (derived carbohydrate-coated, superparamagnetic iron oxide), or mixtures thereof. In some instances, the iron compositions have a pH from about 10 to about 11.1. In other instances, the iron compositions have a neutral pH or a pH of about 7.

In some embodiments, the injectable iron composition, comprises, consists essentially of, or consists of iron, a carbohydrate, a stabilizing agent (e.g., a buffering agent) and water.

The present application also provides methods of making the stable injectable iron composition. In one aspect, a method of making the stable injectable iron composition is provided, the method comprises, consists of, or consists essentially of mixing components such as iron-carbohydrate colloid and water to form a mixture, adding a stabilizing agent to the mixture to form the stable injectable iron composition. The components of the stable injectable iron composition can be added in any order.

In some embodiments, the method of preparing a stable injectable iron composition further includes adding the composition to a container. The container can be a single use vial, ampule or bottle made of glass (e.g., Type I glass, non-treated glass, treated molded glass, etc.) or plastic material (e.g., polypropylene) or a bag, or the container includes a vial having a barrier coated stopper (e.g., 20 mm silicone and/or ethylene tetrafluoroethylene (ETFE) stopper or 32 mm uncoated stopper) and/or an aluminum cap. In other aspects, the method further includes filtering the composition. In yet other embodiments, the method further includes sterilization and/or heat treatment of the composition by terminal sterilization or autoclave.

Methods of treating a disease, disorder, or condition characterized by iron deficiency or dysfunctional iron metabolism are also provided. The method of treatment includes administering to a subject in need of treatment a stable injectable iron composition comprising iron, a carbohydrate, a stabilizing agent and water.

In some instances, diseases, disorders or conditions characterized by iron deficiency or dysfunctional iron metabolism include anemia that is due to impaired iron absorption or poor nutrition or anemia associated with Crohn's Disease; gastric surgery; ingestion of drug products that inhibit iron absorption; and chronic use of calcium. In other instances, the anemia is an iron deficiency anemia, such as that associated with chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidal anti-inflammatory agents, or chronic ingestion of erythropoiesis stimulating agents. In some aspects, the anemia is anemia of chronic disease, such as rheumatoid arthritis; cancer; Hodgkin's leukemia; non-Hodgkin's leukemia; cancer chemotherapy; inflammatory bowel disease; ulcerative colitis thyroiditis; hepatitis; systemic lupus erythematosus; polymyalgia rheumatica; scleroderma; mixed connective tissue disease; Sjogren's syndrome; congestive heart failure/cardiomyopathy; or idiopathic geriatric anemia.

In various embodiments, the method treats restless leg syndrome; blood donation; Parkinson's disease; hair loss; or attention deficit disorder.

In some embodiments, there is an injectable iron composition comprising an iron (III)-hydroxide-sucrose complex; sucrose in an amount greater than 15 mg/mL of the injectable iron composition, a sodium compound comprising sodium acetate, sodium hydroxide, sodium carbonate, sodium bicarbonate or mixtures thereof; and water.

In some embodiments, there is an injectable iron composition comprising an iron (III)-hydroxide-sucrose complex comprising about 1 mg/mL of iron (III)-hydroxide bound to about 15 mg/mL of sucrose; a stabilizing agent comprising about 80 mg/mL of sucrose and about 0.08 mg/mL of sodium hydroxide; and water.

In some embodiments, there is an injectable iron composition comprising an iron (III)-hydroxide-sucrose complex comprising about 2 mg/mL of iron (III)-hydroxide bound to about 30 mg/mL of sucrose; a stabilizing agent comprising about 85 mg/mL of sucrose and about 0.96 mg/mL of sodium hydroxide; and water.

In some embodiments, there is an injectable iron composition comprising an iron (III)-hydroxide-sucrose complex comprising about 1 mg/mL of iron (III)-hydroxide; about 95 mg/mL of sucrose; about 0.08 mg/mL of sodium hydroxide; and water.

In some embodiments, there is an injectable iron composition comprising an iron (III)-hydroxide-sucrose complex comprising about 2 mg/mL of iron (III)-hydroxide; about 115 mg/mL of sucrose; about 0.96 mg/mL of sodium hydroxide; and water.

In some embodiments, there is a method of making a stable injectable iron composition, the method comprising mixing an iron (III)-hydroxide-sucrose complex comprising about 1 mg/mL of iron (III)-hydroxide bound to about 15 mg/mL of sucrose with a stabilizing agent comprising about 80 mg/mL of sucrose and about 0.08 mg/mL of sodium hydroxide and water to form the stable injectable iron composition.

In some embodiments, there is a method of making a stable injectable iron composition, the method comprising mixing an iron (III)-hydroxide-sucrose complex comprising about 2 mg/mL of iron (III)-hydroxide bound to about 30 mg/mL of sucrose with a stabilizing agent comprising about 85 mg/mL of sucrose and about 0.96 mg/mL of sodium hydroxide and water to form the stable injectable iron composition.

In some embodiments, there is a method of making a stable injectable iron composition, the method comprising mixing an iron (III)-hydroxide-sucrose complex comprising about 1 mg/mL of iron (III)-hydroxide with about 95 mg/mL of sucrose and about 0.08 mg/mL of sodium hydroxide and water to form the stable injectable iron composition.

In some embodiments, there is a method of making a stable injectable iron composition, the method comprising mixing an iron (III)-hydroxide-sucrose complex comprising about 2 mg/mL of iron (III)-hydroxide with about 115 mg/mL of sucrose and about 0.96 mg/mL of sodium hydroxide and water to form the stable injectable iron composition.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

All scientific and technical terms used herein have meanings commonly used in the art unless otherwise specified. The definitions provided herein are to facilitate understanding of certain terms used frequently herein and are not meant to limit the scope of the present disclosure It is noted that, as used in this specification and the appended claims, the singular forms "a," "an," and "the," include plural referents unless expressly and unequivocally limited to one referent. Thus, for example, reference to "a stabilizing agent" includes one, two, three or more stabilizing agents.

As used in this specification and the appended claims, the term "or" is generally employed in its sense including "and/or" unless the content clearly dictates otherwise.

Unless defined otherwise, all technical and scientific terms used herein have the same meaning as is commonly understood by one of skill in the art to which the disclosure(s) belong. All patents, patent applications, published applications and publications, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

The term "composition(s)" refers to an aggregate material formed from two or more substances, ingredients or constituents; the way in which a whole or mixture is made up. When referring to pharmaceutical drug products, a composition is often called "formulation(s)".

The term "impurity" refers to a constituent, component or ingredient which impairs the purity of pharmaceutical active ingredient or pharmaceutical composition.

The term "injectable" or "injectable composition," as used herein, means a composition that can be drawn into a container and injected intravenously, subcutaneously, intramuscularly, intra-arterially, intra-cardiac, intrathecally, epidurally, intraparenchymally, intraperitoneally, intracerebroventricularly, intraventricularly, or the like into an animal (e.g., human).

The term "reference listed drug" refers to an approved drug product to which generic versions are compared to show that they are bioequivalent.

The term "stability" refers to capability of a pharmaceutical active ingredient or pharmaceutical composition to remain within a specific criteria or specification(s).

The term "stable", as used herein, means remaining in a state or condition that is suitable for administration to a patient and without undergoing a substantial change in the potency of the active agent in the formulation over the specified time period. In some embodiments, the injectable iron composition of the current application is considered stable if the iron colloidal composition can maintain its integrity and required release kinetics at the level specified on the label for the maximum anticipated shelf-life (e.g., the time period from the date of manufacture until administration to the animal) under environmental conditions likely to be encountered in actual use. Typically, stability can be determined following the FDA guidelines, for example, Guidance for Industry: Drug Stability Guidelines (p. 1-48), Dec. 9, 2008. In some embodiments, compositions are stable when maintained at room temperature for at least 6 months, usually at least 12 months, and generally for at least 18, 24, 36 or 48 months. In some embodiments, the compositions are also preferably stable over more extended periods of time when stored at 25° C. A substantial change in critical quality attributes is one which affect the product quality, from the target concentration for the specified period of time. Critical quality attributes include, for example, Mn, Mw and PDI of the compositions of this application. In some embodiments, unless indicated otherwise, a stable composition is one which retains at least about 85%, or at least about 90%, or at least about 95%, or at least about 99% of the original amount of the colloidal iron (III) carbohydrate complex composition in that state (e.g., not substantially precipitated, not substantially degraded or not substantially adsorbed to the container) for a period of at least six months. In some embodiments, unless indicated otherwise, the stable composition is one which retains at least about 85%, or at least about 90%, or at least about 95%, or at least about 99% of the original amount of the colloidal iron (III) carbohydrate complex composition in that state (e.g., not substantially precipitated, not substantially degraded or not substantially adsorbed to the container) for a period of at least one year. In some embodiments, unless indicated otherwise, the stable composition is one which retains at least about 85%, or at least about 90%, or at least about 95%, or at least about 99% of the original amount of the colloidal iron (III) carbohydrate complex composition in that state (e.g., not substantially precipitated, not substantially degraded or not substantially adsorbed to the container) for a period of two years. In some embodiments, the stable composition has a potency range of 95% to 105% or 90% to 110% of the labeled quantity for a period up to 2 years.

The term "buffer" as used herein refers to a solution that resists changes in pH when acid or alkali is added to it. Examples of simple buffering agents used in aqueous buffers are citric acid, acetic acid, sodium or potassium dihydrogen phosphate ($NaH_2PO_4$ or $KH_2PO_4$), disodium or dipotassium hydrogen phosphate ($Na_2HPO_4$ or $K_2HPO_4$), sodium carbonate ($Na_2CO_3$), sodium bicarbonate ($NaHCO_3$), potassium carbonate ($K_2CO_3$), potassium bicarbonate ($KHCO_3$), CHES (N-Cyclohexyl-2-aminoethanesulfonic acid), and boronic acid (borate). Examples of other common buffering agents are TAPS (3-{[tris(hydroxymethyl)methyl]amino}propanesulfonic acid), Bicine (N,N-bis(2-hydroxyethyl)glycine), Tris (tris(hydroxymethyl)methylamine), Tricine (N-tris(hydroxymethyl)methylglycine), HEPES (4-2-hydroxyethyl-1-piperazineethanesulfonic acid), TES (2-{[tris (hydroxymethyl)methyl] amino}ethanesulfonic acid), MOPS (3-(N-morpholino)propanesulfonic acid), PIPES (piperazine-N,N'-bis(2-ethanesulfonic acid)), Cacodylate 5 (dimethylarsinic acid), SSC (saline sodium citrate), IVIES (2-(N-morpholino)ethanesulfonic acid), and Succinic acid (2(R)-2-(methylamino)succinic acid).

The carriers and excipients and other components of the pharmaceutical compositions must be "pharmaceutically acceptable" in the sense of being compatible with the other ingredients of the formulation and not deleterious to the recipient thereof. Thus, the term "pharmaceutically acceptable salt" references salt forms of the active compounds which are prepared with counter ions which are non-toxic under the conditions of use and are compatible with a stable formulation. For compounds which contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. Salts derived from pharmaceutically acceptable organic non-toxic bases include salts of primary, secondary, and tertiary amines, substituted amines including naturally occurring substituted amines, cyclic amines, ethanolamine, 2-diethylaminoethanol, amino acids and its derivatives including but not limited to lysine, arginine, glycine and histidine.

The term "pharmaceutically acceptable carrier or excipient" means a carrier or excipient that is useful in preparing a pharmaceutical composition that has an acceptable side-effect profile and serves to provide a medium for the storage or administration of the active component(s) under the conditions of administration for which the composition is formulated or used. The carrier or excipient is compatible with the other ingredients of the formulation and not deleterious to the recipient thereof. A "pharmaceutically acceptable carrier or excipient" as used in the specification and claims includes both one and more than one such carrier or excipient. Pharmaceutically acceptable carriers are determined in part by the particular composition being administered, as well as by the particular method used to administer the composition. There are a wide variety of suitable formulations of pharmaceutical compositions of the present disclosure (see, e.g., Remington's Pharmaceutical Sciences, 20th ed., 2018, supra).

The term "Mn" refers to the number average molecular weight which is the statistical average molecular weight of all the polymer chains in the sample, and is defined by:

$$Mn = \frac{\sum N_i M_i}{\sum N_i}$$

where Mi is the molecular weight of a chain and Ni is the number of chains of that molecular weight. Mn can be predicted by polymerization mechanisms and is measured by methods that determine the number of molecules in a sample of a given weight; for example, colligative methods such as, for example, by analytical ultracentrifugation, gel permeation chromatography, or the like. Particular methods of determining Mn is described in Zou, Peng, et al. "Physicochemical Characterization of Iron Carbohydrate Colloid Drug Products," The AAPS Journal, Vol. 19, No. 5, September 2017, pp. 1359-1376.

The term "Mw" refers to weight average molecular weight and is defined as $$Mw = \frac{\sum N_i M_i^2}{\sum N_i M_i},$$

where Mi is the molecular weight of a chain and Ni is the number of chains of that molecular weight. Compared to Mn, Mw takes into account the molecular weight of a chain in determining contributions to the molecular weight average. The more massive the chain, the more the chain contributes to Mw. Mw is determined by methods that are sensitive to the molecular size rather than just their number, such as light scattering techniques. Mw and Mn can also be measured using methods known in the art including, but not limited to, size exclusion chromatography (SEC), analytical ultracentrifugation (AUC), gel permeation chromatography (GPC), or the like. A particular method of determining the molecular weights is described e.g., in P. Geisser, M. Baer, and E. Schaub, Arzneim.-Forsch./Drug Res. 42 (II), 12, 1439-1452 (1992).

The term "PDI" refers to the polydispersity index of a polymer and is used as a measure of the broadness of a molecular distribution of a polymer. PDI is defined by the ratio of Mw to Mn.

The term "tonicity adjusting agents" refers to agents used to modify the osmolality of a formulation to bring it closer to the osmotic pressure of body fluids such as blood or plasma. Provided that the compositions are physiologically compatible, the compositions do not require any particular osmolality. Thus, the compositions can be hypotonic, isotonic, or hypertonic. Typically, the pharmaceutical compositions of the present application, in some embodiments, have an osmolality of about 200 mOsm/L, 250, 300, 350, 400, 450, 500, 550, to about 600 mOsm/L to reduce pain, irritation and tissue damage. The tonicity of the pharmaceutical compositions can be adjusted by adjusting the concentration of any one or more of a tonicity agent, a co-solvent, complexing agent, buffering agent, or excipient. Suitable tonicity adjusting agents include, but are not limited to, anhydrous and hydrous forms of NaCl, dextrose, sucrose, xylitol, fructose, glycerol, sorbitol, mannitol, KCl, $CaCl_2$, $MgCl_2$ or a combination thereof.

The pH of the iron composition can be adjusted to a recited pH range or target pH by the addition of an acid or acidic salt or base or basic salt, as appropriate. For instance, the pH may be adjusted with an alkalinizing agent such as an alkali metal hydroxide such as NaOH, KOH, or LiOH, or an alkaline earth metal hydroxide, such as $Mg(OH)_2$ or $Ca(OH)_2$, or a carbonate.

The term "pharmaceutical composition" is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients described herein.

The term "ready-to-use composition" refers to an injectable composition containing the active drug in solution at the required concentration and volume, presented in the final container (syringe, vial, ampule, bottle, infusion bag, or elastomeric device), and ready to be administered to a patient in need thereof, for example, without the need for further dilution.

The term "therapeutically effective amount" refers to an amount of an agent sufficient to prevent treat conditions such as for example, low in vivo iron blood levels, anemia or the like when administered alone or as one of multiple dosages to a subject. The "therapeutically effective amount" will vary depending on the formulation, the severity of the condition, the age, general health condition, and weight of the subject to be treated.

The term "pre-mixed", as used herein, means a pharmaceutical composition that is already mixed from the point of pre-sale packaging and/or manufacture and does not require reconstitution or dilution before administration to a subject.

The term "single-use container" refers to a sealed pharmaceutically prepared container holding a drug product in a sterile environment that is intended to be used in a single operation of transferring the entire contents or substantially entire contents. It should be recognized that the single-use container is generally preservative-free and that if multiple transfers are attempted, they should be completed in a short duration, i.e., less than about 8-10 hours from the first breach of the sterile environment. In some aspects the single-use container may be used to administer all of its contents to one subject in need thereof. In some aspects the single-use container may be used to administer its contents to more than one subject in need thereof.

As used herein, the term "mixing" refers to admixing, contacting, blending, stirring or allowing to admix, mix, blend, stir or the like.

The term "dissolved oxygen" refers to oxygen that is found in the aqueous carrier of the compositions. Distinguished from dissolved oxygen is the headspace oxygen. As used herein, the term "headspace oxygen" refers to the oxygen that is found in the headspace volume of the sealed container comprising the composition.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

The headings below are not meant to limit the disclosure in any way; embodiments under any one heading may be used in conjunction with embodiments under any other heading.

Iron Compositions

This application relates to the development of stable injectable iron compositions comprising iron, a carbohydrate, a stabilizing agent and water. More specifically, in some embodiments, the present disclosure is directed to a stable, ready-to-use (RTU) pharmaceutical formulation or composition of iron sucrose for parenteral use, such as, for example, via injection, or intravenous infusion, with or without an intravenous pump.

In some embodiments, the ready-to-use or ready to administer stable injectable compositions of the current application reduce time in preparation and are convenient to administer. These compositions are premade and minimize potential medication errors that may occur in mixing the compositions, as well as choosing the proper delivery vehicle for infusion.

In some embodiments, the compositions and methods described herein utilize a suitable alkali solution and/or buffering agent and/or sucrose to stabilize the formulation, and to prevent or reduce the aggregation and precipitation of the iron-sucrose complex. It is understood by those skilled in the art that the excipients described herein serve only as a non-limiting example of iron carbohydrate stabilization agent. Non-limiting agents include buffers such as carbonate buffers, sugar carbohydrates, sugar-lipids, sodium gluconate or a mixture thereof. The iron compositions of the current application contain an active pharmaceutical ingredient that pertains to the category of iron carbohydrates, such as for example, iron sucrose for parenteral iron therapy.

In some embodiments, the iron in the stable injectable iron compositions of the present application comprise elemental iron. Elemental iron includes the amount of iron present in the iron-carbohydrate complex or iron-carbohydrate colloid. Elemental iron includes, for example, iron in its $3^+$ oxidation state. For example, in the iron-sucrose complex or iron-sucrose colloid of the ready-to-use formulation, in some embodiments, the amount of elemental iron is 1 mg/mL or 2 mg/mL. Carbohydrates useful in preparing the iron compositions of this disclosure include a monosaccharide, a disaccharide, an oligosaccharide or a polysaccharide. Examples of useful monosaccharides include without limitation glucose, galactose, fructose or mixtures thereof. Useful disaccharides include, for example, sucrose, lactose, maltose, or mixtures thereof. Useful oligosaccharide can include raffinose, stachyose, verbascose or mixtures thereof. Various polysaccharides include starch, a starch derivative, dextran, cellulose, glycogen or mixtures thereof. For example, starch derivatives can include a dextrin comprising a maltodextrin, a maltose syrup or a glucose syrup or mixtures thereof. In some embodiments, maltodextrins can have a DE (dextrose equivalent) of between 3 and 20. In some embodiments, the maltose syrup can have a DE of greater than 50 (e.g., 52). In some embodiments, the glucose syrup can have a DE of greater than 20 (e.g., 42). In some aspects, the monosaccharides can include dihydroxyacetone, glyceraldehyde, erythrose, ribose, ribulose, sorbose, xylose, arabinose, fructose, glucose, galactose, mannose, or mixtures thereof. In other aspects, useful disaccharides can be selected from sucrose, maltose, cellobiose, gentiobiose, isomaltose, melibiose, primeverose, rutinose, trehalose, lactose or mixtures thereof. In other embodiments, the carbohydrates useful in preparing the stable iron sucrose composition of this disclosure include a modified saccharide, or a modified disaccharide, or a modified oligosaccharide or a modified polysaccharide. Examples of these modified saccharides include without limitation, hydroxyethyl starch, deferoxamine, dextran aldehyde, dextran methacrylate, acid modified starch, sucralose, acetyl thiosucrose or any other modified saccharide. The preferred carbohydrate is sucrose.

In some embodiments, the iron component of the iron composition of the present application has surface interaction with the carbohydrate component to allow the iron to be in solution as colloidal particles to form the iron-carbohydrate colloid. In some embodiments, iron colloids can comprise an iron oxyhydroxide or iron oxide core that is complexed with the carbohydrate. In some embodiments, sucrose can interact with the iron core to have the iron-sucrose complex or iron suerose colloid iron-sucrose colloid.

In many embodiments, the elemental iron of the stable injectable iron compositions of this disclosure and the carbohydrate forms a colloidal iron (III) carbohydrate complex. Colloidal iron (III) carbohydrate complexes usually comprise spheroidal iron-carbohydrate nanoparticles, the core of each particle being an iron-oxyhydroxide gel, which is surrounded by a shell of the carbohydrate that stabilizes the iron-oxyhydroxide cores (see e.g., Bo G. Danielson, J Am Soc Nephrol 15: S93-S98, 2004). In other embodiments, the colloidal iron (III) carbohydrate complex comprises an iron monosaccharide complex, an iron disaccharide complex, an iron oligosaccharide complex, an iron polysaccharide complex or combinations thereof. In yet other embodiments, the iron polysaccharide complex comprises iron carboxymaltose, iron sucrose, iron polyisomaltose, iron polymaltose, iron gluconate, iron sorbitol, iron hydrogenated dextran, iron derisomaltose (e.g., ferric derisomaltose or iron isomaltoside), or mixtures thereof. In various aspects, the stable injectable compositions comprise iron carboxymaltose (iron carboxymaltodextrin), iron sucrose, iron polyisomaltose, iron polymaltose, iron gluconate, iron sorbitol, iron hydrogenated dextran, iron derisomaltose (e.g., ferric derisomaltose or iron isomaltoside), ferumoxytol (derived carbohydrate-coated, superparamagnetic iron oxide), or mixtures thereof.

Examples of iron carbohydrate complexes include iron monosaccharide complexes, iron disaccharide complexes, iron oligosaccharide complexes, and iron polysaccharide complexes, such as: iron carboxymaltose, iron sucrose, iron polyisomaltose (iron dextran), iron polymaltose (iron dextrin), iron gluconate, iron sorbitol, iron hydrogenated dextran, which may be further complexed with other compounds, such as sorbitol, citric acid and gluconic acid (for example iron dextrin-sorbitol-citric acid complex and iron sucrose-gluconic acid complex), and mixtures thereof.

In some embodiments, as described in U.S. application Ser. No. 15/958,930 to Helenek et al. incorporated herein by reference as if set forth in full, the iron carbohydrate complex can be iron carboxymaltose complex, iron mannitol complex, iron polyisomaltose complex, iron polymaltose complex, iron gluconate complex, iron disaccharide complex, iron oligosaccharide complex, iron sorbitol complex, or an iron hydrogenated dextran complex. In some embodiments, the iron carbohydrate complex is an iron polyglucose sorbitol carboxymethyl ether complex. In some other embodiments, the iron carboxymaltose complex contains about 24% to about 32% elemental iron, about 25% to about 50% carbohydrate, and is about 100,000 Daltons to about 350,000 Daltons. In various embodiments, the iron carboxymaltose complex is obtained from an aqueous solution of iron (III) salt and an aqueous solution of the oxidation product of one or more maltodextrins using an aqueous hypochlorite solution at a pH value within the alkaline range, wherein, when one maltodextrin is applied, its dextrose equivalent lies between 5 and 20, and when a mixture of several maltodextrins is applied, the dextrose equivalent lies between 5 and 20 and the dextrose equivalent of each individual maltodextrin contained in the mixture lies between 2 and 20. In other embodiments, the iron carboxymaltose complex has a chemical formula of $[FeO_x(OH)_y(H_2O)_z]_n[\{(C_6H_{10}O_5)_m(C_6H_{12}O_7)\}_l]_k$, (wherein preferably the indices x, y, z, n, m, l and k provide for a weight average molecular weight of about 100,000 Daltons to about 350,000 Daltons), and where more preferably n is about $10^3$, m is about 8, l is about 11, and k is about 4; contains about 28% elemental iron; and has a molecular weight of about 150,000 Da. In many other embodiments, the iron carboxymaltose complex is polynuclear iron (III)-hydroxide 4(R)-(poly-(1→4)-O-α-glucopyranosyl)-oxy-2(R),3(R),5(R),6-tetrahydroxy-hexanoate.

In various embodiments, the iron carbohydrate complex comprises an iron core with a mean iron core size of no greater than about 9 nm. In some embodiments, the mean iron core size is at least about 1 nm but no greater than about 9 nm; at least about 3 nm but no greater than about 7 nm; or at least about 4 nm but not greater than about 5 nm. The iron core size can be determined by, for example, Transmission Electron Microscopy (TEM), X-ray Diffraction (XRD), Atomic Force Microscopy (AFM), or Mossbauer spectroscopy as described in Zou, Peng, et al. "Physicochemical Characterization of Iron Carbohydrate Colloid Drug Products," The AAPS Journal, Vol. 19, No. 5, September 2017, pp. 1359-1376.

In various embodiments, the mean size of a particle of the iron carbohydrate complex is no greater than about 35 nm. In some embodiments, the particle mean size is no greater than about 30 nm. In some embodiments, the particle mean size is no greater than about 25 nm. In some embodiments, the particle mean size is no greater than about 20 nm; no greater than about 15 nm; no greater than about 10 nm; or at least about 6 nm but no greater than about 7 nm. The iron core size can be determined by, for example, Transmission Electron Microscopy (TEM), X-ray Diffraction (XRD), Atomic Force Microscopy (AFM), or Mossbauer spectroscopy as described in Zou, Peng, et al. "Physicochemical Characterization of Iron Carbohydrate Colloid Drug Products," The AAPS Journal, Vol. 19, No. 5, September 2017, pp. 1359-1376.

In some embodiments, iron polymaltose (iron dextrin) has a carbohydrate component which contains glucose molecules joined by α-1,4 linkages. In other cases, iron polyisomaltose has a carbohydrate component which contains long chains of α-1,6-linked glucose residues (i.e., chains of isomaltoses), as in dextran. However, as distinct from dextran, polyisomaltose is linear while dextran is a branched carbohydrate. In many cases, the iron polyisomaltose complex is substantially non-immunogenic and substantially non-cross-reactive with anti-dextran antibodies. As used herein, the term "iron carbohydrate complex is substantially non-immunogenic" includes that the iron carbohydrate complex results in a low risk of anaphylactoid/hypersensitivity reactions, wherein a low risk is an incidence of adverse events lower than iron dextran. As also used herein, the term "substantially no cross reactivity with anti-dextran antibodies" includes that it does not exhibit substantial binding to anti-dextran antibodies.

Iron ferumoxytol also known as derived carbohydrate-coated, superparamagnetic iron oxide relates to an iron complex where ferumoxytol includes a polyglucose sorbitol carboxymethyl ether-coated non-stoichiometric magnetite.

An example of iron sucrose injectable solution is Venofer® (Iron Sucrose Injection, USP), which is 20 mg/mL composed of the active pharmaceutical ingredient (API) polynuclear iron (III)-hydroxide in sucrose having a molecular weight of approximately 34,000 to 60,000 Daltons (Da) and a proposed structural formula of: $[Na_2Fe_5O_8(OH) \cdot 3(H_2O)]_n \cdot m(C_{12}H_{22}O_{11})$, where n is the degree of iron polymerization and m is the number of sucrose molecules associated with the polymerized iron (III)-hydroxide and are in the range of providing said molecular weight.

Venofer® is indicated for the treatment of iron deficiency anemia in patients with chronic kidney disease (CKD). In a mammal body, the poly-nuclear iron (III)-hydroxide-sucrose structure is dissociated into iron and sucrose following intravenous administration, and the iron is transported as a complex with transferrin to target cells including erythroid precursor cells. The iron in the precursor cells is incorporated into hemoglobin as the cells mature into red blood cells. In addition to Venofer®, other parenteral iron compositions approved in the United States include iron dextran (e.g., InFed®, Dexferrum®), sodium ferric gluconate complex in sucrose (Ferrlecit®), and ferric carboxymaltose injection (Injectafer®). Those approved in the UK also includes iron sucrose (Sucrofer®, UK Claris).

Ferric derisomaltose (e.g., ferric derisomaltose or iron isomaltoside) is another form of iron compound used in the treatment of iron deficiency. This drug is a complex of iron (III) hydroxide and derisomaltose. The latter is an iron carbohydrate oligosaccharide that works to release iron. The molecular formula of this iron carbohydrate complex is $C_{18}H_{34}FeO_{16}^{+3}$. Specifically, ferric derisomaltose is an iron carbohydrate complex with a matrix structure composed of interchanging layers of ferric hydroxide and the carbohydrate derisomaltose. Derisomaltose contains linear, hydrogenated isomaltooligosaccharides with an average molecular weight of 1000 Da. Ferric derisomaltose has an average molecular weight of 155,000 Da and has the following empirical formula: $\{FeO(1-3X)(OH)(1+3X)(C_6H_5O_{73}-)X\}$, $(H_2O)T$, $(C_6H_{10}O_6)R(-C_6H_{10}O_5-)Z(C_6H_{13}O_5)R$, $(NaCl)Y$ wherein $X=0.0311$; $T=0.25$; $R=0.14$; $Z=0.49$; $Y=0.14$.

In many aspects, in injectable iron compositions described in this disclosure the stabilizing agent comprises an alkalinizing agent, a buffering agent, sucrose or a mixture thereof. In many aspects, the stable injectable iron compositions described in this disclosure also include an agent that can be selected from an alkali solution, a buffering agent or sucrose. Useful alkali solutions include without limitation sodium hydroxide, potassium hydroxide, calcium hydroxide or a mixture thereof. Buffering agents useful as stabilizing agents in the current iron compositions of the present disclosure include acidic buffers and basic buffers. Stabilizing agents include, but are not limited to, hydrochloric acid, sodium acetate, acetic acid, sodium citrate, citric acid, sodium hydroxide, sodium carbonate, sodium bicarbonate, potassium carbonate, potassium bicarbonate, calcium carbonate, calcium bicarbonate or a mixture thereof. Other useful buffering agents that can be used as stabilizing agents include, but are not limited to, sucrose, polyisomaltose, sorbitol, citric acid, polymaltose, gluconate, chondroitin sulfate, carboxymaltose, mannitol, polyglucose sorbitol carboxymethyl ether, isomaltoside, derisomaltose, citrate, L-histidine, histidine, glycine, arginine, tyrosine, lysine or a mixture thereof.

The stabilizing agent in the current iron compositions of the present disclosure reduce changes to pH, Mw, Mn, density, T75, and/or PDI over a period of time compared to iron compositions which do not comprise the stabilizing agent. For example, in some embodiments, unless indicated otherwise, the stable composition is one which retains at least about 85%, or at least about 90%, or at least about 95%, or at least about 99% of the original amount of the colloidal iron (III) carbohydrate complex composition in that state (e.g., not substantially precipitated, not substantially degraded or not substantially adsorbed to the container) for a period of two years. In some embodiments, the stable composition has a potency range of 95% to 105% or 90% to 110% of the labeled quantity for a period up to 2 years.

In some aspects, the stable injectable iron compositions include elemental iron, the carbohydrate comprises sucrose, and the stabilizing agent comprises at least one of sodium compound, L-histidine, or sucrose. The sodium can be provided by, for example, sodium hydroxide, sodium chloride or sodium gluconate. The sodium compound can also stabilize the iron in the composition.

In some embodiments, the total amount of carbohydrate referred to herein (e.g., total sucrose) includes the carbohydrate ligand that is complexed with or bound to the iron and the amount that is not complexed with or bound to the iron, for example, as described in the Examples. In some embodiments, the carbohydrate that is not complexed with the iron can be added to the already carbohydrate-iron complex. In various embodiments, the iron compositions described in this application contain elemental iron (from about 1.0 to about 2.0 mg/mL), total sucrose (from about 20 to about 195 mg/mL), Na ion (from about 2 to about 708 mM or 0.08 to about 28.3 mg/mL as NaOH) to adjust tonicity and/or as a stabilizer, and a buffer comprised of L-histidine (from about 0 to about 0.9 mg/mL) to maintain the pH in the range of from about 10 to about 11.1 and Water for Injection (Q.S.) as the vehicle. In various embodiments, excipients include sucrose, NaOH and L-histidine and they can, in some embodiments, be included within the limit concentration for intravenous compositions within the limits indicated by the FDA Inactive Ingredient Database. For example, the FDA's database lists as no more than 0.09% w/v mg for histidine, 2.83% w/v for NaOH and 19.5% w/v for sucrose for intravenous solutions.

In some aspects, the stable injectable compositions include elemental iron in an amount of 1.0 mg, total sucrose in an amount of 57.5 mg/mL, sodium hydroxide in an amount of 0.08 mg/mL, and optionally L-histidine in an amount of 0.75 mg/mL. In various embodiments the stable injectable compositions described in this disclosure have a total volume of 1 mL, which allows for their application to a patient suffering from anemia related disease, disorder, or condition as an intravenous push, thereby avoiding drawbacks resulting from prolonged intravenous infusions. However, in some embodiments, it is possible to dilute the injectable composition having a total volume of 1 mL with saline or dextrose 5% in water, which is suitable for injection intravenously (IV) to replace lost fluids and provide carbohydrates to the body, also known as D5W solution. Dextrose 5% in water, in some embodiments, can be used to treat low blood sugar (hypoglycemia), insulin shock, or dehydration.

In some embodiments, the stable iron composition of the present application can have iron nano sized particles having an average particle size range of about 7 nm to about 25 nm. For example, the stable iron composition of the present application can have whole iron nano sized particles having an average particle size range of about 8.0 nm, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.1, to about 10.2 nm. The iron core size can be determined by, for example, Dynamic Light Scattering (DLS), Atomic Force Microscopy (AFM), or Mossbauer spectroscopy as described in Zou, Peng, et al. "Physicochemical Characterization of Iron Carbohydrate Colloid Drug Products," The AAPS Journal, Vol. 19, No. 5, September 2017, pp. 1359-1376.

In various embodiments, the elemental iron of the stable injectable iron compositions of this disclosure and the carbohydrate form a colloidal iron (III) carbohydrate complex. The elemental iron (III) in the colloidal iron carbohydrate complex can be in an amount from about 0.25 mg/mL to about 20 mg/mL (e.g., 1 mg/mL to about 2 mg/mL or 1 mg/mL to about 5 mg/mL). In some embodiments, the amount of elemental iron can be in a range from about 1 mg/mL, 1.1, 1.2, 1.3, 1.4, 1.5, 1.6, 1.7, 1.8, 1.9, 2 mg/mL, 3 mg/mL 4 mg/mL, 5 mg/mL, 6 mg/mL, 7 mg/mL, 8 mg/mL, 9 mg/mL, 10 mg/mL, 11 mg/mL, 12 mg/mL, 13 mg/mL, 14 mg/mL, 15 mg/mL, 16 mg/mL, 17 mg/mL, 18 mg/mL, 19 mg/mL to about 20 mg/mL.

The carbohydrate can be in the composition in an amount of from about 3 mg/mL to about 250 mg/mL (e.g., about 5 mg/mL to about 200 mg/mL). In some embodiments, the carbohydrate can be in the composition in an amount of from about 3 mg/mL to about 250 mg/mL (e.g., about 5 mg/mL to about 200 mg/mL) per 1 mg or 2 mg of iron. In some embodiments, this can include the total amount of carbohydrate (e.g., total sucrose) that is the carbohydrate complexed with or bound to the iron and the amount that is not complexed with or bound to the iron, for example as shown in Table IV. In some embodiments, the carbohydrate can be part of the stabilizing agent, which can be sucrose in an amount from about 3 mg/mL to about 250 mg/mL (e.g., about 5 mg/mL to about 195 mg/mL).

In some aspects, sucrose, which can be a stabilizing agent as well in some embodiments, can be in the composition in a range from about 5 mg/mL, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42.5, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 to about 200 mg/mL.

In some aspects, sucrose, which can be a stabilizing agent as well in some embodiments, can be in the composition in a range from about 5 mg/mL, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42.5, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 to about 200 mg/mL per 1 mg or 2 mg of iron.

In some embodiments, the stabilizing agent in the composition comprises an alkalinizing agent, a buffering agent or sucrose. The alkalinizing agent can comprise sodium hydroxide, potassium hydroxide, calcium hydroxide or a combination thereof. The alkalinizing agent can be in the composition in an amount of about 0.025 mg/mL to about 80 mg/mL (e.g., about 0.08 mg/mL to about 28.3 mg/mL). In some embodiments, the alkalinizing agent can be in the composition in an amount of about 0.025 mg/mL to about 80 mg/mL (e.g., about 0.08 mg/mL to about 28.3 mg/mL) per 1 mg/mL or 2 mg/mL of iron. In various embodiments, the ready-to-use (RTU) IV infusion includes elemental iron in an amount from about 1 mg/mL to about 2 mg/mL (from about 18 mM to about 36 mM), sucrose in an amount from about 15 mg/mL to about 195 mg/mL (from about 44 mM to about 570 mM), $Na^+$ ion as supplied by NaOH in an amount from about 0.08 to about 28.3 mg/mL (from about 2 mM to about 708 mM) and L-histidine in an amount from about 0 to about 0.9 mg/mL (from about 0 to about 6 mM) or 0 to about 1.5 mg/mL (from about 0 to about 10 mM).

In some embodiments, the L-histidine can be in the composition in an amount from about 0 to about 0.9 mg/mL (from about 0 to about 6 mM) or 0 to about 1.5 mg/mL (from about 0 to about 10 mM) per 1 mg/mL or 2 mg/mL of iron.

For example, the stabilizing agent (e.g., sodium hydroxide) can be in the composition in a range from about 0.08 mg/mL, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, to about 28.3 mg/mL.

In some embodiments, the iron-carbohydrate complex or iron-carbohydrate colloid can be stabilized with the stabilizing agent (e.g., sodium compound, histidine, and/or carbohydrate, such as sucrose or mixtures thereof) by its addition to the iron-carbohydrate complex or iron-carbohydrate colloid. While not wishing to be bound to any particular theory, it is believed, in some embodiments, that the sodium compound and/or unbound sucrose can stabilize the iron-sucrose complex or iron-sucrose colloid. For example, the stabilizing agent can reduce or prevent the aggregation of iron sucrose resulting from an increase in the weight average molecular weight, decrease in pH, change in iron species, and precipitation of the iron-sucrose complex.

The w/w or w/v ratio of elemental iron (e.g., 1 mg or 2 mg of iron) to carbohydrate (e.g., sucrose) in the stabilized iron compositions of the present application can be in the range from about 1:16, w/w or w/v, 1:20, 1:25, 1:30, 1:35, 1:40, 1:45, 1:50, 1:55, 1:60, 1:65, 1:70, 1:75, 1:80, 1:85, 1:90, 1:95, 1:100, 1:105, 1:110, 1:115, 1:120, 1:125, 1:130, 1:135, 1:140, 1:145, 1:150, 1:155, 1:160, 1:165, 1:170, 1:175, 1:180, 1:190, 1:195, to about 1:200 w/w or w/v.

In some embodiments, the buffering agent in the composition can comprise sodium carbonate, sodium bicarbonate, potassium carbonate, potassium bicarbonate, calcium carbonate, calcium bicarbonate, L-histidine, glycine, arginine, tyrosine, lysine or a combination thereof. The buffering agent can be in the composition in an amount of 0.125 mg/mL to about 5 mg/mL or 0.125 mg/mL to about 20 mg/mL or about 1 mg/mL to about 1.4 mg/mL, 1.5 mg/mL, 1.6 mg/mL, 1.7 mg/mL, 1.8 mg/mL, 1.9 mg/mL to about 2.0 mg/mL In some embodiments, the buffering agent comprises L-histidine and the L-histidine is in the composition in a range from about 0 mg/mL, 0.125, 0.25, 0.1, 0.2, 0.3, 0.4, 0.5, 0.6, 0.7, 0.8, to about 0.9 mg/mL.

In a particular embodiment, the colloidal iron (III) carbohydrate complex comprises iron sucrose, where the iron sucrose includes elemental iron (III) in an amount from about 1 mg/mL to about 2 mg/mL and sucrose in an amount from about is from about 14 to about 31 mg/mL. In some aspects, the sucrose in the colloidal iron (III) carbohydrate complex before additional sucrose is added as a stabilizing agent can be in a range from about 1 mg/mL, 2, 3, 4, 5, 6, 7, 8, 9, 10, 11, 12, 13, 14, 15, 16, 17, 18, 19, 20, 21, 22, 23, 24, 25, 26, 27, 28, 29, or 30 to about 31 mg/mL.

In some aspects, the sucrose in the colloidal iron (III) carbohydrate complex before additional sucrose is added as a stabilizing agent can be in a range from about 1 mg sucrose per 1 mg iron, 2 mg sucrose, 3 mg sucrose, 4 mg sucrose, 5 mg sucrose, 6 mg sucrose, 7 mg sucrose, 8 mg sucrose, 9 mg sucrose, 10 mg sucrose, 11 mg sucrose, 12 mg sucrose, 13 mg sucrose, 14 mg sucrose, 15 mg sucrose, 16 mg sucrose, 17 mg sucrose, 18 mg sucrose, 19 mg sucrose, 20 mg sucrose, 21 mg sucrose, 22 mg sucrose, 23 mg sucrose, 24 mg sucrose, 25 mg sucrose, 26 mg sucrose, 27 mg sucrose, 28 mg sucrose, 29 mg sucrose, 30 mg sucrose to about 31 mg sucrose per 1 mg of iron.

The stabilizing agent of sodium hydroxide can be added to the compositions in an amount from about 0.07, or about 0.08 to about 28.3 mg/mL or to about 0.96 mg/mL, L-histidine can be in an amount from about 0 to about 0.9 mg/mL and additional sucrose can be added as a stabilizing agent in an amount from about 5 to about 195 mg/mL.

In other embodiments, the elemental iron in the stable injectable compositions can be in an amount of 1 mg/mL, sucrose, whether bound or unbound, can be in an amount from about 20 to about 95 mg/mL, sodium hydroxide can be in an amount from about 0.08 to about 1.84 mg/mL and L-histidine can be in an amount from about 0 to about 1.6 mg/mL. In various embodiments, the amount of sucrose in the stable injectable compositions of this disclosure can be greater than 15 mg/mL. In yet other embodiments, the stable injectable iron composition includes sucrose in the colloidal iron (III) carbohydrate complex in an amount that can vary from about 15 to about 30 mg/mL and elemental iron in an amount that can be from about 1 to about 2 mg/mL, wherein further the amount of sucrose that can be added to the already formed colloidal iron (III) carbohydrate complex as a stabilizing agent can vary from about 5 to about 195 mg/mL, the amount of sodium hydroxide can vary from about 0.07 to about 28.3 mg/mL or to about 0.98 mg/mL and the amount of L-histidine can vary from about 0 to about 1.6 mg/mL. In some embodiments, the stable injectable iron composition includes sucrose in the colloidal iron (III) carbohydrate complex in an amount that can vary from about 15 to about 30 mg/mL and elemental iron in an amount that can be from about 1 mg/mL to about 20 mg/mL.

In a particular embodiment, the iron composition comprises the colloidal iron (III) carbohydrate complex, which comprises iron sucrose in an amount from about 1 mg/mL, 2 mg/mL, 3 mg/mL, 4 mg/mL, 5 mg/mL, 6 mg/mL, 7 mg/mL, 8 mg/mL, 9 mg/mL to about 10 mg/mL.

In one particular embodiment, the active pharmaceutical ingredient (API) in the iron composition comprises polynuclear iron (III)-hydroxide in sucrose having a molecular weight of approximately 34,000 to 60,000 Daltons (Da) and a proposed structural formula:

$$[Na_2Fe_5O_8(OH)\cdot 3(H_2O)]_n \cdot m(C_{12}H_{22}O_{11})$$

where n is the degree of iron polymerization and m is the number of sucrose molecules associated with the polymerized iron (III)-hydroxide. The sucrose in the polynuclear iron (III)-hydroxide complex can be in a range from about 0.5 mg/mL, 1, 1.5, 2, 2.5, 3, 4, 5, 6, 7, 8, 9, 10, 11, 12, 13, 14, 15, 16, 17, 18, 19, 20, 21, 22, 23, 24, 25, 26, 27, 28, 29, 30 to about 31 mg/mL. The stabilizing agent sodium hydroxide can be present in the iron composition of these embodiments in an amount from about 0.07, or about 0.08 to about 28.3 mg/mL or to about 0.96 mg/mL.

In various aspects, the stable injectable compositions described in this disclosure have a pH from about 10 to about 11.5 and a physiological osmolarity. In some embodiments, the injectable compositions of the present application have an osmolality of about 200 mOsm/L, 250, 300, 345, 350, 400, 450, 480, 500, 550, to about 600 mOsm/L to reduce pain, irritation and tissue damage.

The pH of the injectable iron composition can be adjusted using a suitable acid. Examples of suitable acids include, but are not limited to, sulfuric acid, nitric acid, hydrochloric acid, phosphoric acid, acetic acid, citric acid, lactic acid, carboxylic acid, sulfonic acid or combinations thereof or the like.

The pH of the injectable iron composition can be adjusted using a suitable base. Examples of suitable bases include, but are not limited to, sodium hydroxide, sodium carbonate, sodium bicarbonate, calcium hydroxide, calcium carbonate, potassium hydroxide, or combinations thereof or the like.

In some embodiments, the pH can be in a range from about 9.5, 9.6, 9.7, 9.8, 9.9, 10, 10.1, 10.2, 10.3, 10.4, 10.5, 10.6, 10.7, 10.8, 10.9, 11.0, 11.1, 11.2, 11.3, 11.4 to about 11.5. The average molecular weight (Mw) of the injectable compositions of this disclosure can vary from about 34 kDa to about 60 kDa. In various aspects, the number average molecular weight (Mn) of these injectable compositions can vary from about 24 kDa to about 60 kDa. The resulting polydispersity index of these injectable compositions can vary from about 1.0, 1.1, 1.2, 1.3, 1.4, 1.5, 1.6 to about 1.7. In some embodiments, the injectable iron compositions of this disclosure have a density of about 1.027 to about 1.047 g/mL or about 1.037 to about 1.058 g/mL for about 3 months, 4, 5, 6, 7, 8, 9, 10, 11, 12, 13, 14, 15, 16, 17, 18, 19, 20, 21, 22, 23, 24, 36 or about 48 months.

In some embodiments, there is potential toxicity resulting from increase in reduction of Fe (III) into Fe (II) species in injectable compositions comprising iron carbohydrate complexes, for example colloid iron-sucrose complexes. To minimize conversion of Fe (III) to Fe (II) and to ensure product quality, stabilizing agents are added so that in some embodiments, the amount of elemental Fe (II) in these iron injectable compositions can vary from about 0.01% to about 0.4% wt/v and in other embodiments, from about 0.4% to about 1.7% wt/wt. In some embodiments, amount of elemental Fe (II) can vary in a range from about 0.4%, 0.5, 0.6, 0.7, 0.8, 0.9, 1.0, 1.1, 1.2, 1.3, 1.4, 1.5, 1.6 to about 1.7% wt/v The stability of the stable iron compositions of the current application, in some embodiments, can be compared to an existing FDA approved injectable iron formulation (Venofer®) using an in vitro controlled release test for trivalent iron (T75) for demonstration of therapeutic equivalency over time. The T75 reduction kinetics of iron from Fe+3 to Fe+2 can be tested as described in U.S. Pat. No. 6,911,342 to Helenek et al. herein incorporated by reference. In various embodiments, the time required for 75% of elemental iron (III) to be released from the iron injectable compositions (also known as T75) can vary from about not more than 20 minutes through the shelf-life of 24 months.

In many embodiments the storage stability of the injectable iron compositions can be about 24 months. In some embodiments, the stability of the injectable iron compositions can be about 3 months, 4, 5, 6, 7, 8, 9, 10, 11, 12, 13, 14, 15, 16, 17, 18, 19, 20, 21, 22, 23 or 24 months. In some embodiments, the stability of the injectable iron compositions can be about 3 months, 4, 5, 6, 7, 8, 9, 10, 11, 12, 13, 14, 15, 16, 17, 18, 19, 20, 21, 22, 23 or 24 months and the compositions have no detectable precipitates form. In yet other aspects, the stable injectable iron compositions of this disclosure can be at least one of a preservative-free composition, a sterile composition, or a ready-to-use injectable aqueous composition.

Container

In various embodiments, the injectable iron sucrose composition is disposed in a container. The container can have a variety of volumes. Typically, the container can have a volume of from about 1 mL to about 250 mL. In some examples, the container can have a volume of from about 1 mL, 5, 10, 20, 30, 40, 50, 60, 70, 80, 90, 100, 110, 120, 130, 140, 150, 160, 170, 180, 190, 200, 210, 220, 230, 240 to about 250 mL. In other embodiments, the volume of the container can be from about 250 mL, 300, 350, 400, 450 to about 500 mL. In many aspects, useful containers for the iron compositions of this disclosure include a single use vial, bottle, ampule, bag or any type of container which can hold the desired volume of the iron composition of the present application in a sterile condition. In other aspects, the container can comprise a vial having a barrier coated stopper and/or an aluminum cap. In some embodiments, the vial or ampule comprises glass (e.g., Type I glass) or plastic material (e.g., polypropylene). In other cases, the container for the iron compositions of this disclosure can be made of a variety of materials. Non-limiting materials for the container can include glass, a plastic (e.g., polyethylene, polypropylene, polyvinyl chloride, polycarbonate, etc.), the like, or a combination thereof that can both prevent or reduce oxygen penetration and minimize aluminum, heavy metals and anions contamination to the composition. In certain embodiments, the container is fabricated from multilayered plastic (PL 2501, PL 2040), also known as a galaxy container, a plastic container primarily for intravenous use. In yet other cases, the container can be a bag, which can be PVC- or polypropylene-based.

In other aspects, the container can be fabricated from glass as a single use vial, for example, a Type I glass vial for injectable products. In other aspects, the container can be a bag having from about 10 mL to about 250 mL. In some aspects, the pharmaceutical compositions of this disclosure can also be stored in glass vials or ampules, for example, single use 10 mL glass vials or ampules.

In some embodiments, the composition comprising iron, a carbohydrate, a stabilizing agent and water can be provided in a bag, syringe, vial, or bottle that can hold a volume of 1 mL, 5, 10, 20, 30, 40, 50, 60, 70, 80, 90, 100, 110, 120, 130, 140, 150, 160, 170, 180, 190, 200, 210, 220, 230, 240 to about 250 mL. The composition can comprise, for example, 1 mg/mL of elemental iron or 2 mg/mL of elemental iron and be in a ready to use formulation that is in a 100 mL bottle or bag containing, for example, a carbohydrate, a stabilizing agent and water. The composition bottle or bag can have a stopper (e.g., uncoated or coated bromobutyl stopper, or uncoated or coated chlorobutyl stopper) and/or a vent disposed therein, which is configured to receive a tube set that can be vented or unvented. The user can, in some embodiments of the ready-to-use iron composition, spike the stopper and connect the vented or unvented tube to the bag or bottle and administer the composition to a patient in need of iron treatment. The administration can be with an IV pump or without an IV pump.

In some embodiments, the iron compositions of the present application are stable in a vial, bottle or bag for an extended period of time at normal storage conditions. In certain embodiments, the iron compositions of the present application are stable at about 25° C.±2° C., 30° C.±2° C., 40° C.±2° C., 60° C.±2° C. at 60-75±5% RH for at least 6 months, usually at least 12 months, and generally for at least 18, 24, 36 or 48 months.

As previously discussed, the pH range for an iron carbohydrate IV dosage form varies from about 10 to about 11.5. This pH may disrupt the plastic coating or silicon coating inside the glass container and aluminum, heavy metals and anions could leach during the shelf life of the product, especially over prolonged storage of the product. Elemental impurities monitored in the finished drug products described in this disclosure include without limitation Cd, Pb, As, Hg, Co, V, Ni, Tl, Au, Pd, Ir, Os, Rh, Ru, Se, Ag, Pt, Li, Sb, Ba, Mo, Cu, Sn, and Cr. In some embodiments, the iron carbohydrate composition comprises 0.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, or 4.9, to about 5.0 ppb of these impurities. In some embodiments, the iron carbohydrate composition comprises elemental impurities in amounts prescribed by International Council for Harmonization (ICH) guidance for industry Q3D Elemental Impurities (ICH Q3D).

Headspace Oxygen

In certain embodiments, the compositions further comprise within the container, headspace gas that includes oxygen in an amount of from about 0.5% v/v to about 5.0% v/v, or from about 0.5% v/v to about 4.0% v/v, or from about 0.5% v/v to about 3.5% v/v, from about 0.5% v/v to about 3.0% v/v, or from about 0.5% v/v to about 2.5% v/v, or from about 0.5% v/v to about 2.0% v/v, or from about 0.5% v/v to about 1.5% v/v, or from about 0.5% v/v to about 1.0% v/v, or in some cases from about 0.1% v/v to about 0.5% v/v, or from about 0.1% v/v to about 0.4% v/v, or from about 0.1% v/v to about 0.3% v/v, or from about 0.1% v/v to about 0.2% v/v. For the sake of clarity and the ease of discussion and measurement, these values are taken for the iron composition at the time of its manufacture ("time zero" data point), or during and up to 1 month from time zero. Additional time points beyond the 1 month from time zero data point may provide similar headspace oxygen levels.

Without wishing to be bound by a particular theory, the dissolved oxygen levels and the head space oxygen levels within a sealed container of iron compositions described herein may reach an equilibrium at some time point during its shelf-life. Such equilibrium may be maintained for a very short time, i.e., for a few seconds, or for a very long time, i.e., for several months. Such equilibrium may on occasion be disturbed by simple agitation. Therefore, it should be recognized that dissolved oxygen levels and headspace oxygen levels may fluctuate from one time point to another in terms of absolute numbers. However, the numbers are expected to stay within the ranges disclosed herein. Occasionally, one number (e.g., dissolved oxygen) may exceed or fall out of a certain range (e.g., from about 0.5 to about 3.0 PPM) at a 15 day time point but may fall within that range at some other time point (e.g., 30 day time point, or later). Therefore, in some aspects, the ranges, subranges, and specific data points disclosed and discussed herein are suitable for time points beyond the time zero- and 1-month time points. In one aspect, the time points could be extended to from about 2 months, 3 months, 6 months, 9 months, 12 months, 15 months, 18 months, and about 24 months.

In some cases, the total amount of oxygen in the sealed container may be an appropriate measure to evaluate the stability of the iron compositions. In many embodiments, the compositions described in this application are not oxygen sensitive. In certain embodiments, the dissolved oxygen level varies from about atmospheric to about 0.5 mg/L.

The amount of oxygen present in the headspace of the container can be controlled by filling the headspace with an inert gas, such as nitrogen or argon. Alternatively, the head space oxygen may be controlled by vacuum operation without using an inert gas. In another aspect, the head space oxygen may be controlled by a combination of vacuum operation and inert gas overlay. In one particular aspect, the head space oxygen is controlled by repeated pulses of vacuum and inert gas overlay in tandem such that the process may start first with vacuum operation followed by inert gas overlay followed by vacuum operation. The combination of vacuum operation and inert gas overlay (or inert gas overlay and vacuum operation) is considered one pulse when both steps are used together. A typical head space control operation may comprise from one to eight pulses. Typically, there could be two, three, four, or five pulses. Each pulse could last from about one tenth of one second to five seconds or from five to fifteen seconds when conducted by automated high-speed equipment custom designed for this specific purpose. In some embodiments, the pulse may last from about 0.1 to about 2.0 seconds. In some embodiments, the pulse may last from about 0.1 to about 1.0 seconds, or from about 0.1 to about 0.4 seconds. When done using manual methods, each pulse could take up to 30-60 seconds or longer.

During a manufacturing process, in one embodiment, dissolved oxygen levels are controlled via sparging with an inert gas. Additionally, a blanket of inert gas (e.g., nitrogen, argon, helium) can be maintained throughout manufacturing and storage to control atmospheric oxygen exposure, while an opaque container (stainless steel or amber glass) is selected to protect the formulation from exposure to light.

In some embodiments, the iron composition is preservative-free. As used herein, preservative-free includes compositions that do not contain a preservative. Thus, the composition does not contain, for example, benzalkonium chloride, methyl, ethyl, propyl or butylparaben, benzyl alcohol, phenylethyl alcohol, or benzethonium. The pH of the iron composition varies from about 10 to about 11.5, the iron composition can exhibit antimicrobial properties (e.g., antibacterial properties) in the absence of a preservative at this alkaline pH.

In some embodiments, one or more antioxidants can be incorporated into the injectable pharmaceutical composition described in this disclosure. Antioxidants can be introduced into the pharmaceutical composition to inhibit or delay potential oxidation of the active ingredient. Examples of antioxidants that may also be present in the injectable pharmaceutical composition, include but are not limited to, acetone sodium bisulfate, ascorbate, ascorbic acid, alpha-tocopherol, bisulfate sodium, butylated hydroxy anisole, butylated hydroxy toluene, cystein, cysteinate HCl, dithionite sodium, gentisic acid, gentisic acid ethanolamine, glutamate monosodium, formaldehyde sulfoxylate sodium, metabisulfite potassium, metabisulfite sodium, monothioglycerol, propyl gallate, sulfite sodium, thioglycolate sodium, or a combination thereof.

In some embodiments, one or more preservatives can be incorporated into the injectable pharmaceutical composition described in this disclosure. Preservatives can be introduced into a pharmaceutical solution to kill bacteria, yeast and mold.

A number of preservatives are available which can kill or prevent the growth of commonly encountered contaminants; these contaminants include, but are not limited to the bacteria *P. aeruginosa, E. coli* and *S. aureus*; the yeast *C. albicans*; and the mold *A. brasiliensis.*

The presence of at least one preservative, in some embodiments, allows for the injectable pharmaceutical composition to be used over a period of at least 2 days, 7 days, even one month or more once the container holding the composition is broached. The injectable pharmaceutical composition has a minimum broached vial antimicrobial effectiveness of at least 1 day and, in some cases, a broached vial antimicrobial effectiveness includes 7 days or more.

The incorporation of a preservative or preservatives within the pharmaceutical composition should not hinder the solubility of the iron composition and the final compositions are still able to pass a test method complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

In some embodiments at least one preservative is present in the pharmaceutical composition and can be selected from a group comprising but not limited to: m-cresol, chlorocresol, parabens including but not limited to methylparaben, ethyl paraben, propylparaben, butylparaben, their derivatives, and salts, chlorobutanol, quaternary ammonium compounds, their derivatives, and salts including benzethonium chloride, benzalkonium chloride, boric acid, benzyl alcohol, cetylpyridinium chloride, cetrimide, phenol, phenyl ethanol, phenoxyethanol or mixtures thereof.

The preservative or preservatives are present in an amount which is effective to impart the desired preservative characteristics and allows the final composition to comply with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

Method of Preparing the Iron Composition

The stable injectable iron compositions of the present application can be made by mixing iron with a carbohydrate, and water to form a mixture and adding a stabilizing agent to the mixture to form the stable injectable iron composition.

In some embodiments, the iron composition of the present application can have the iron core bound to the carbohydrate ligand to form the iron-carbohydrate complex or iron-carbohydrate colloid. The iron core can be, for example, a polynuclear iron-oxyhydroxide core that can be bound to the carbohydrate ligand by Van der Waals forces, non-ionic hydrogen bonds, ionic hydrogen bonds, and/or coordinative bonds.

The stable iron composition of the present application can be prepared using a commercially available iron-carbohydrate complex or iron-carbohydrate colloid that water, and a stabilizing agent discussed herein can be mixed with to form the stable ready-to-use or ready-to-administer iron compositions of the current application. Suitable commercially available iron-carbohydrate complexes or iron-carbohydrate colloids that provide the source of elemental iron that can be used to make the stable iron compositions of the current application are listed in Table A below.

TABLE A

| Ligand(s) | Trade Names | Common Names | Ligand Description |
|---|---|---|---|
| High-molecular-weight iron dextran; LMWID: Low-molecular-weight iron dextran. | | | |
| Sucrose | Venofer ®<br>Fesin ®<br>Ferrivenin ® | Iron sucrose<br>Iron saccharate<br>Saccharated iron oxide | Disaccharide |
| Dextran (polyisomaltose) | Imferon ® (HMWID)<br>Dexferrum ® (HMWID)<br>INFeD/Cosmofer ® (LMWID) | Iron dextran | Polysaccharide, maltose units 1 → 6-1 inked |
| Sorbitol and citric acid | Jectofer ® | Iron sorbitex | Monosaccharide and carboxylic acid |
| Dextrin (polymaltose) | Amylofer ® | Dextriferron<br>Iron polymaltose | Polysaccharide, maltose units 1 → 4-1 inked |
| Gluconate and sucrose | Ferrlecit ® | Sodium ferric gluconate | Carboxylic acid and disaccharide |
| Chondroitin sulfate | Blutal ® | Iron chondroitin sulfate | Sulfated poly-glycosaminoglycan, alternating N-acetylgalactosamine and glucuronic acid |
| Carboxymaltose | Inj ectafer ®/Ferinject ® | Ferric carboxymaltose | Poly-(1-4)-a-D-glucopyranosyl-( 1 → 4)-D-gluconate |
| Polyglucose sorbitol carboxymethyl ether and mannitol (excipient) | Feraheme ® | Ferumoxytol | Polysaccharide, maltose units 1 → 6-1 inked, hydrogenated, and carboxymethylated, and monosaccharide |
| Isomaltoside 1000/derisomaltose, and citrate | Monoferric ®/Monofer ® | Iron isomaltoside 1000<br>Ferric derisomaltose | Oligosaccharide, maltose units 1 → 6-1 inked, hydrogenated, and carboxylic acid |

The commercially available iron-carbohydrate complexes or iron-carbohydrate colloids listed in Table A are available from the following manufacturers listed in Table B below.

TABLE B

| Trade Names | Manufacturer |
|---|---|
| Venofer ® | Vifor (International) AG, Switzerland/American Regent, Shirley, New York, U.S.A. |
| Fesin ® | XIEON LIFESCIENCES PVT LTD, India |
| Ferrivenin ® | AOBIOUS, Gloucester, Mass., U.S.A. |
| Imferon ® (HMWID) | SHREYA LIFE SCIENCES PVT LTD, India |
| Dexferrum ® (HMWID) | American Regent, Shirley, New York, U.S.A. |
| INFeD/Cosmofer ® (LMWID) | Pharmacosmos Therapeutics Inc., Morristown, NJ, U.S.A. |
| Jectofer ® | AstraZeneca UK Ltd., United Kingdom |
| Amylofer ® | Vifor (International) AG, Switzerland |
| Ferrlecit ® | Sanofi Aventis, France |
| Blutal ® | Dainippon Pharmaceutical Co., Ltd. Japan |
| Inj ectafer ®/Ferinject ® | Vifor (International) AG, Switzerland/American Regent, Shirley, New York, U.S.A. |
| Feraheme ® | AMAG Pharmaceuticals, Inc., Waltham, Mass., U.S.A. |
| Monoferric ®/Monofer ® | Pharmacosmos Therapeutics Inc., Morristown, NJ, U.S.A. |

Referring to Table A above, iron sucrose contains the disaccharide sucrose as a ligand, e.g., a low-molecular-weight carbohydrate. The drug product contains 20 mg elemental iron/mL and approximately 30% sucrose w/v (300 mg/mL), e.g., 15 mg sucrose/mg iron. The drug product has a pH of 10.5 to 11.1. The proposed structural formula is $[Na_2Fe_5O_8(OH)\cdot 3(H_2O)]_n\cdot m(C_{12}H_{22}O_{11})$. Sodium ferric gluconate comprises the sodium salt of a ferric ion carbohydrate complex in an alkaline aqueous solution with 12.5 mg iron/mL and approximately 20% sucrose w/v, e.g., 16 mg sucrose/mg iron. In contrast to iron sucrose, the drug product has a pH 7.7-9.7. The structural formula is considered to be $[NaFe_2O_3(C_6H_{11}O_7)(C_{12}H_{22}O_{11})_5]_{n\sim 200}$. According to this formula, it contains one gluconate, also a low-molecular-weight ligand per two iron or 1.7 mg gluconate/mg iron.

Low-molecular-weight iron dextran contains 50 mg iron/mL. The pH of the solution is between 4.5 to 7.0. The content of iron(III)-hydroxide dextran complex is 312.5 mg/mL. The dextran content is approximately 206 mg/mL or 4.1 mg dextran/mg iron.

Ferric derisomaltose, also referred to as iron isomaltoside 1000, contains 100 mg iron/mL. Isomaltoside 1000 comprises 3-5 glucose units and originates from a chemical modification of isomalto-oligosaccharides present in Dextran 1. Ferric derisomaltose has the following empirical formula: $\{FeO^{(1-3X)}(OH)^{(1+3X)}(C_6H_5O_7{}^{3-})\}_X$, $(H_2O)_T$, $(C_6H_{10}O_6)_R(—C_6H_{10}O_5{}^-)_Z(C_6H_{13}O_5)_R$, $(NaCl)_Y$; X=0.0311; T=0.25; R=0.14; Z=0.49; Y=0.14. The iron carbohydrate complex contains approximately 2.3 mg derisomaltose/mg iron. The iron citrate isomaltoligosaccharide alcohol-hydrate complex, ferric derisomaltose also contains citrate as an additional ligand in a concentration of approximately 10 mg/mL or 0.1 mg citrate/mg iron. The drug product is a solution with pH 5.0-7.0.

Ferric carboxymaltose contains 50 mg iron/mL. The complex has the following empirical formula: $[FeO_x(OH)_y(H_2O)_z]_n[\{(C_6H_{10}O_5)_m(C_6H_{12}O_7)\}_l]_k$, where $n \approx 10^3$, $m \approx 8$, $l \approx 11$, and $k \approx 4$ (l represents the mean branching degree of the ligand). The ligand carboxymaltose is obtained from maltodextrin by oxidation. The drug product is a solution with pH 5.0-7.0. The complex contains approximately 75 mg carboxymaltose/mL (approximately 1.5 mg carboxymaltose/mg iron).

Ferumoxytol contains 30 mg of iron/mL. The complex is an iron oxide coated with polyglucose sorbitol carboxymethylether. The chemical formula of ferumoxytol is $Fe_{5874}O_{8752}$—$C_{11719}H_{18682}O_{9933}Na_{414}$. Based on this formula the complex contains approximately 0.97 mg carbohydrate/mg iron. Polyglucose sorbitol carboxymethylether is a dextran with low degree of branching (1-2%), partly carboxymethylated at positions C-2, C-3, or C-4 in the glucan backbone and with a reduced, non-carboxymethylated C-1 chain end unit. The ferumoxytol drug product is formulated with mannitol (1.5 mg mannitol/mg iron). It has a pH of 6 to 8.

The commercially available iron-carbohydrate complexes or iron-carbohydrate colloids listed in Table A have the following iron-carbohydrate content and pH listed in Table C.

TABLE C

| Product | Carbohydrate(s) | Iron Content (mg Fe/mL) | Approximate Carbohydrate Content (mg/mL) | Approximate Carbohydrate Content (mg/mg Fe) | pH |
|---|---|---|---|---|---|
| Iron Sucrose | Sucrose | 20 | 300 | 15 | 10.5-11.1 |
| Sodium ferric Gluconate | Sucrose Gluconate | 12.5 | 195 22 | 16 1.7 | 7.7-9.7 |
| Iron dextran | Dextran | 50 | 206 | 4.1 | 4.5-7.0 |
| Ferric derisomaltose | Derisomaltose Citrate | 100 | 230 10 | 2.3 0.1 | 5.0-7.0 |
| Ferric carboxymaltose | Carboxymaltose | 50 | 75 | 1.5 | 5.0-7.0 |
| Ferumoxytol | Polyglucose sorbitol carboxymethylether Maltose (excipient) | 30 | 29 44 | 0.97 1.5 | 6-8 |

The commercially available iron-carbohydrate complexes or iron-carbohydrate colloids listed in Table A have the following physico-chemical properties listed in Table D below.

TABLE D

| Product | Molecular Weight (kDa) | Estimated Particle Size (nm) | ^Zeta Potential | Crystalline Structure |
|---|---|---|---|---|
| Iron sucrose | 34-60 42-44 252 140 | 8.3 (PDI 0.192) | (mV) pH 11.03*: −28.15 | 2-line ferrihydrite Ferrihydrite and Lepidocrocite Akageneite 2-line ferridydrite-like No clear identification |
| Sodium ferric gluconate | 289-440 37.5 200 164 | 8.6 (PDI 0.244) | pH 7.4: −29.70 pH 8.36*: −29.10 | 2-line ferrihydrite Ferrihydrite and Lepidocrocite Akageneite |
| Iron dextran | 165 | 12.2 (PDI 0.149) | pH 6.4*: −15.30 pH 7.31: −17.25 | Akageneite |
| Ferric derisomaltose | 155 63-69 150 | 9.9 (PDI 0.182) | pH 6.3*: −22.0 pH 735: −21.05 | Akageneite |
| Ferric carboxymaltose | ≈150 145-155 233 | 23.1 (PDI 0.07) | pH 5.36: 3.68 pH 7.26: −8.52 | Akageneite |
| Ferumoxytol | 750 172-188 731 276 | 23.6 (PDI 0.143) | pH 6.6: −43.20 pH 7.36: −30.55 | Magnetite/Maghemite Magnetite Maghemite |

*Non-adjusted pH; PDI: polydispersity index. Data from Funk et. al Int. J. Mol. Sci. 2022, 23, 2140.
^Zeta Potential can be used to predict the stability of particles in suspension.

The iron-carbohydrate complexes or iron-carbohydrate colloids listed in Table A can be used to provide the source of elemental iron as an iron-carbohydrate complex or iron-carbohydrate colloid for the stable iron compositions of the present application. The iron-carbohydrate complex or iron-carbohydrate colloid can be mixed with water and a stabilizing agent to obtain the stable iron compositions of the present application. Stabilizing agents include, but are not limited to, hydrochloric acid, sodium acetate, acetic acid, sodium citrate, citric acid, sodium hydroxide, sodium carbonate, sodium bicarbonate, potassium carbonate, potassium bicarbonate, calcium carbonate, calcium bicarbonate, sucrose, sucrose gluconate, sorbitol, citric acid, polymaltose (dextrins), gluconate, chondroitin sulfate, carboxymaltose (carboxymaltodextrin), maltose, mannitol, polyglucose sorbitol carboxymethyl ether, isomaltoside, derisomaltose, citrate, L-histidine, histidine, glycine, arginine, tyrosine, lysine or a mixture thereof. In some embodiments, the stabilizing agent can be a sodium compound, for example, sodium acetate, sodium chloride, sodium hydroxide, sodium carbonate, sodium bicarbonate or mixtures thereof.

Such mixing may cause one or more chemical reactions (e.g., additional colloidal formation); however, the mixing of components in the iron composition can be in any order. In some embodiments, the stable injectable composition of the present application can be prepared by mixing an iron carbohydrate colloid with water to form a mixture to which a stabilizing agent is added to form the stable injectable iron composition. In some embodiments, mixing can be done where the carbohydrate (e.g., sucrose) is added to water to form a mixture of water and carbohydrate and then the stabilizing agent (e.g., sodium hydroxide) is added to that mixture and then the iron is added to that mixture with or without an additional stabilizing agent to form the stable injectable iron composition (e.g., at a pH range of from about 10.1-11.1). The injectable iron composition can then be filtered and/or autoclaved and placed in a container (e.g., vial, ampule, I.V. bottle, IV bag, etc.) and sealed.

In many cases, the carbohydrate, which itself can be a stabilizing agent, can be a monosaccharide, a polysaccharide, such as for example, a disaccharide, or an oligosaccharide. The monosaccharide can be glucose, galactose, fructose or mixtures thereof. Useful disaccharides include, for example, sucrose, lactose, maltose, or mixtures thereof. Useful oligosaccharide can include, ferric derisomaltose or iron isomaltoside, raffinose, stachyose, verbascose or mixtures thereof. Various polysaccharides include starch, a starch derivative, dextran, cellulose, glycogen or mixtures thereof. For example, starch derivatives can include a dextrin comprising a maltodextrin, a maltose syrup or a glucose syrup or mixtures thereof. In some aspects, the monosaccharides can include dihydroxyacetone, glyceraldehyde, erythrose, ribose, ribulose, sorbose, xylose, arabinose, fructose, glucose, galactose, mannose, or mixtures thereof. In other aspects, useful disaccharides can be selected from sucrose, maltose, cellobiose, gentiobiose, isomaltose, melibiose, primeverose, rutinose, trehalose, lactose or mixtures thereof.

In some embodiments, the iron present in the stable injectable iron sucrose compositions is elemental iron. In various embodiments, the elemental iron of the stable injectable iron compositions of this disclosure and the carbohydrate forms a colloidal iron (III) carbohydrate complex. In many cases, the colloidal iron (III) carbohydrate complex comprises an iron monosaccharide complex, an iron disaccharide complex, an iron oligosaccharide complex, an iron polysaccharide complex or combinations thereof. In yet other embodiments, the iron polysaccharide complex comprises iron carboxymaltose, iron sucrose, iron polyisomaltose, iron polymaltose, iron gluconate, iron sorbitol, iron hydrogenated dextran, iron derisomaltose (e.g., ferric derisomaltose or iron isomaltoside) or mixtures thereof. In various aspects, the stable injectable compositions comprise iron carboxymaltose, iron sucrose, iron polyisomaltose, iron polymaltose, iron gluconate, iron sorbitol, iron hydrogenated dextran, iron derisomaltose (e.g., ferric derisomaltose or iron isomaltoside), ferumoxytol (derived carbohydrate-coated, superparamagnetic iron oxide) or isomers thereof or mixtures thereof.

The stable iron compositions of the present application include isomers, such as structural isomers, enantiomers or diastereomers, of the carbohydrates mentioned herein and their derivatives. Isomers include two or more compounds with the same formula but a different arrangement of atoms in the molecule and different properties.

In some embodiments, the iron present in the injectable iron sucrose composition comprises polymerized iron (III)-hydroxide complex, polynuclear iron (III)-hydroxide complex, iron (III)-hydroxide sucrose complex, polymerized iron (III)-hydroxide colloid, polynuclear iron (III)-hydroxide colloid, or iron (III)-hydroxide sucrose colloid or a combination thereof. In some embodiments, this can provide 1 mg or 2 mg of elemental iron.

In many aspects, the stable injectable iron compositions described in this disclosure also include a stabilizing agent that can be selected from an alkalinizing agent, a buffering agent and/or sucrose. Useful alkalinizing agents (e.g., alkali solutions) include without limitation sodium hydroxide, potassium hydroxide, calcium hydroxide or a mixture thereof. Buffering agents useful as stabilizing agent include sodium carbonate, sodium bicarbonate, potassium carbonate, potassium bicarbonate, calcium carbonate, calcium bicarbonate or a mixture thereof. Other buffering agents can be selected from L-histidine, histidine, glycine, arginine, tyrosine or lysine.

In some embodiments, the stabilizing agent (e.g., sodium hydroxide) can be added in an amount from about 1 mM/mL, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, to about 50 mM/mL of the iron composition.

In some embodiments, the stabilizing agent (e.g., histidine) can be added in an amount from about 0.25 mg/mL, 0.5, 0.75, 0.8, 1.0, 1.25, 1.5, to about 2.0 mg/mL of the iron composition.

Buffering agents are used to adjust the pH of the injectable iron compositions in this alternative aspect as well. The pH of the compositions is, in some cases, between, 9.5 and 11.5 or 10 and 11.5. In other aspects, the pH of the compositions is between 10.5 and 11.1.

In some embodiments, the stable injectable iron compositions of the present application can be made from a starting material that can be an injectable iron-(III)-hydroxide-sucrose complex that is then stabilized to obtain the stable injectable iron compositions of the present application. A suitable injectable iron-(III)-hydroxide-sucrose complex that can be used as a starting material in the present application can be, for example, 1 mg or 2 mg of Venofer® obtained from Vifor (International) AG, Switzerland/American Regent, Shirley, N.Y., U.S.A. In some embodiments, the iron-(III)-hydroxide-sucrose complex or iron-(III) oxyhydroxide-sucrose complex starting material can be prepared by reacting ferric salts (e.g., ferric chloride) with an inorganic base (e.g., NaOH) at pH 3.5 to 7.0 to provide ferric oxyhydroxide, which is then added to a solution of sucrose followed by adjusting the pH of the mixture between 9.0 and 13.0 with an inorganic base to yield the iron-(III)-hydroxide-sucrose complex, which then can be isolated by partial concentration of the aqueous mixture and precipitation, by addition of an organic solvent or mixture thereof to isolate the iron-(III)-hydroxide-sucrose complex.

Methods of making iron-(III)-hydroxide-sucrose complex or iron-(III) oxyhydroxide-sucrose complex used as the starting material in the present application are described in many references including U.S. Pat. Nos. 7,964,568; 7,674,780; 8,053,470; U.S. Publication No. 20080167266; U.S. Publication No. 20180147238; U.S. Pat. Nos. 8,030,480 and 8,053,470. These entire disclosures are herein incorporated by reference into the present disclosure. The iron-(III)-hydroxide-sucrose complex or iron-(III) oxyhydroxide-sucrose complex can then be mixed with the stabilizing agent and water as discussed herein to obtain the stable injectable iron composition of the present application.

In some embodiments, a method of making a stable injectable iron composition is provided, the method comprising mixing iron-(III)-oxyhydroxide or iron-(III)-hydroxide with sucrose to form a mixture; and adding a stabilizing agent to the mixture to form the stable injectable iron composition.

It will be understood that, in some embodiments, the components of the iron composition (e.g., iron, carbohydrate, stabilizing agent, water and or and/or iron-carbohydrate complex) can be mixed in any order. After, mixing and the additions of the components, the pharmaceutical iron composition can be sterilized, for example, by filtering it through one or more filters (e.g., 0.22 µm sterile filters). The sterilized iron composition can then be filled in the appropriate container (e.g., vial, ampule, bag, etc.) and stoppered and sealed, for example, under a reduced oxygen headspace of either 5% oxygen (balance nitrogen) or 10% oxygen (balance nitrogen). In certain embodiments, the oxygen headspace in the container can vary over a range from about atmospheric to about 0.5 mg/L. In some embodiments, the iron composition can be packaged in a pharmaceutically acceptable container, such as an intravenous bag, syringe, vial or ampule. The pH of the compositions is, in some aspects, between 9.5 to 11.5 or 10 and 11.5.

The present disclosure also relates to methods for preparing such compositions. In this other aspect, the term "pre-mixed", as used herein, means a pharmaceutical iron composition that is already mixed from the point of manufacture and does not require dilution or further processing before administration. In various embodiments, pre-mixed injection can be a single-use, ready-to-use, iso-osmotic solution for intravenous administration. No further dilution would be required. Prior to administration, the pre-mixed injection should be visually inspected for particulate matter and discoloration prior to administration, whenever solution and container permit. A pre-mixed injection is normally a clear, amber to dark brown colored solution.

In some cases, the iron composition is added to a container that can be a single use container, for example, a single use vial or ampule or the container comprises a vial having a barrier coated stopper and/or an aluminum cap. As described above, the vial, ampule, bag can be made of glass or plastic based materials.

In various embodiments, the iron compositions prepared by mixing iron with a carbohydrate and water to form a mixture and adding a stabilizing agent to the mixture to form the stable injectable iron composition can be further filtered followed by terminal sterilization and autoclave.

In various embodiments, gamma radiation can be used in the terminal sterilization step, which involves utilizing ionizing energy from gamma rays that penetrate deeply into a vial containing the iron composition of this disclosure. Gamma rays are highly effective in killing microorganisms, they leave no residues, nor do they have sufficient energy to impart radioactivity to the apparatus. Gamma rays can be employed when the iron composition is in a vial, ampule or bag because gamma ray sterilization does not require high pressures or vacuum conditions, and thus the container of the iron composition is not stressed. In some aspects, the vial or ampule can be made of glass or plastic material and, in other aspects, the vial, ampule or bag can be prepared from plastic material, for example, polypropylene.

In other embodiments, electron beam (e-beam) radiation may be used to sterilize the iron composition described in this disclosure. E-beam radiation comprises a form of ionizing energy, which is generally characterized by low penetration and high-dose rates. E-beam irradiation is similar to gamma ray processing in that it alters various chemical and molecular bonds on contact, including the reproductive cells of microorganisms. Beams produced for e-beam sterilization are concentrated, highly charged streams of electrons generated by the acceleration and conversion of electricity.

Autoclaving is usually performed in an autoclave. An autoclave uses pressurized steam as their sterilization agent. The basic concept of an autoclave is to have each item sterilized—whether it is a liquid, plastic ware, or glassware—come in direct contact with steam at a specific temperature and pressure for a specific amount of time. Time, steam, temperature, and pressure are the four main parameters required for a successful sterilization using an autoclave.

The amount of time and temperature required for sterilization of a vial or ampule containing the iron composition can use higher temperatures for sterilization and requires shorter times. The most common temperatures used are 121° C. and 132° C. In order for steam to reach these high temperatures, steam has to be pumped into the chamber at a pressure higher than normal atmospheric pressure. Normal atmospheric pressure is about 101,325 pascals (roughly 14.6959 pounds per square inch). In some embodiments, the vials can be heat treated at temperatures from about 60° C. to about 132° C.

The iron compositions of the present disclosure are preferably packaged in pharmaceutically acceptable containers in many aspects. Pharmaceutically acceptable containers include intravenous vials, ampules and syringes. In some embodiments, the iron compositions of the current disclosure, although not required, can be further diluted in dextrose, saline or a combination thereof.

In some embodiments, it is also desirable to protect the pharmaceutical compositions from light. Therefore, the container may, optionally, further comprise a light barrier. In certain embodiments, the light barrier can be an aluminum over pouch.

In many aspects, the present disclosure also provides methods for preparing sterile pharmaceutical compositions. Examples of suitable procedures for producing sterile pharmaceutical drug products include, but are not limited to, terminal moist heat sterilization, ethylene oxide, radiation (i.e., gamma and electron beam), and aseptic processing techniques. Any one of these sterilization procedures can be used to produce the sterile pharmaceutical compositions described herein.

Sterile pharmaceutical compositions may also be prepared using aseptic processing techniques. Sterility is maintained by using sterile materials and a controlled working environment. All containers and apparatus are sterilized, preferably by heat sterilization, prior to filling. Then, the container is filled under aseptic conditions, such as by passing the composition through a filter and filling the units. Therefore, the compositions can be sterile filled into a container to avoid the heat stress of terminal sterilization. In some embodiments, the iron sucrose compositions of the current application can be heated, for example, from about 60° C. to about 132° C. after placement in the container (e.g., vials) as part of the drug product stabilization and/or the terminal sterilization process.

As stated above, the iron compositions of the present application can be sterile, which includes iron compositions that meet the criteria of sterility according to the US Pharmacopoeia 40-NF 35<71> ("40 USP"). Further regulations for sterility of the final product include the European Pharmacopoeia (Ph. Eur. section 2.6.1), and the Japanese Pharmacopoeia (JP section 54). These sterility methods have been harmonized with the USP methods and results generated under these sources can be considered equivalent to testing conducted according to USP <71>. Preferably, the therapeutically acceptable iron compositions of the present application have been produced by a method which provides assurance of sterility according to the US Pharmacopoeia 40-NF 35<71> or USP 41<71>.

Method of Use of the Iron Compositions

The iron compositions described in this disclosure can be used for the treatment of a disease, disorder, or condition characterized by iron deficiency or dysfunctional iron metabolism. The method of treatment includes administering to a subject in need of treatment a stable injectable iron composition comprising iron, a carbohydrate, a stabilizing agent and water. In some embodiments, the iron composition is administered intravenously and can be injected in a single push over a period ranging from 1 minute to about 150 minutes. In some embodiments, the IV administration can be over a period ranging from about 1 minute, 2, 3, 4, 5, 6, 7, 8, 9, 10, 11, 12, 13, 14, 15, 20, 25, 30, 40, 45, 60, 75, 90, 105, 120, 135 and 150 minutes. In many cases, the injectable iron composition can be administered in a single dosage unit of at least 1 mg/mL of elemental iron, which does not require further dilution, does not require an IV bag or bottle, and does not require an IV tube set or pump. In other embodiments, the injectable iron composition is a single dosage unit of at least 1 mg/mL of elemental iron which can be administered in less than 25 minutes, less than 10 minutes, or less than 5 minutes or less than 1 minute.

There are many diseases, disorders or conditions characterized by iron deficiency or dysfunctional iron metabolism that can be treated with the injectable iron compositions described in this application. For example, in some embodiments, the disease, disorder, or condition is anemia, and, in some cases, the anemia is iron deficiency anemia. In other embodiments, the iron deficiency anemia is associated with chronic blood loss; acute blood loss; chronic kidney disease; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidal anti-inflammatory agents, or chronic ingestion of erythropoiesis stimulating agents or combinations thereof.

In various embodiments, the iron compositions described in this disclosure can be used to treat an anemia which is anemia of chronic disease, such as for example, rheumatoid arthritis; cancer; Hodgkin's leukemia; non-Hodgkin's leukemia; anemia from chemotherapy; inflammatory bowel disease; ulcerative colitis; thyroiditis; hepatitis; systemic lupus erythematosus; polymyalgia rheumatica; scleroderma; mixed connective tissue disease; Sjogren's syndrome; congestive heart failure/cardiomyopathy; or idiopathic geriatric anemia.

In some instances, diseases, disorders or conditions characterized by iron deficiency or dysfunctional iron metabolism is an anemia that is due to impaired iron absorption or poor nutrition or the anemia is associated with Crohn's Disease; gastric surgery; ingestion of drug products that inhibit iron absorption; and chronic use of calcium. In yet other instances, the method of treatment described in this application treats anemia. In some embodiments, the anemia is an iron deficiency anemia, such as that associated with chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidal anti-inflammatory agents, or chronic ingestion of erythropoiesis stimulating agents. In some aspects, the anemia is anemia of chronic disease, such as rheumatoid arthritis; cancer; Hodgkin's leukemia; non-Hodgkin's leukemia; cancer chemotherapy; inflammatory bowel disease; ulcerative colitis thyroiditis; hepatitis; systemic lupus erythematosus; polymyalgia rheumatica; scleroderma; mixed connective tissue disease; Sjogren's syndrome; congestive heart failure/cardiomyopathy; or idiopathic geriatric anemia. In some embodiments, the anemia is due to impaired iron absorption or poor nutrition, such as anemia associated with Crohn's Disease; gastric surgery; ingestion of drug products that inhibit iron absorption; and chronic use of calcium. In various embodiments, the method treats restless leg syndrome; blood donation; Parkinson's disease; hair loss; or attention deficit disorder.

These and other aspects of the present application will be further appreciated upon consideration of the following examples, which are intended to illustrate certain particular embodiments of the application, but they are not intended to limit its scope, as defined by the claims.

EMBODIMENTS

1. An injectable iron composition comprising iron, a carbohydrate, a stabilizing agent and water.

2. The injectable iron composition of embodiment 1, wherein the iron is elemental iron.

The injectable iron composition of embodiment 1, wherein the carbohydrate comprises (i) a monosaccharide, a disaccharide, an oligosaccharide or a polysaccharide; or (ii) a modified monosaccharide, a modified disaccharide, a modified oligosaccharide or a modified polysaccharide.

4. The injectable iron composition of embodiment 2, wherein the elemental iron and the carbohydrate form a colloidal iron (III) carbohydrate complex.

5. The injectable iron composition of embodiment 1, wherein the composition comprises iron carboxymaltose, iron sucrose, iron polyisomaltose, iron dextrin, iron gluconate, iron sorbitol, iron hydrogenated dextran, iron derisomaltose, derived carbohydrate-coated, superparamagnetic iron oxide or isomers thereof or mixtures thereof.

6. The injectable iron composition of embodiment 3, wherein (i) the monosaccharide comprises glucose, galactose, fructose, isomers thereof or mixtures thereof; (ii) the disaccharide comprises sucrose, lactose, maltose or isomers thereof or mixtures thereof; (iii) the oligosaccharide comprises raffinose, stachyose, verbascose or isomers thereof or mixtures thereof; or (iv) the polysaccharides comprise starch, a starch derivative, dextran, cellulose, glycogen or isomers thereof or mixtures thereof.

7. The injectable iron composition of embodiment 3, wherein (i) the monosaccharide comprises dihydroxyacetone, glyceraldehyde, erythrose, ribose, ribulose, sorbose, xylose, arabinose, fructose, glucose, galactose, mannose, or isomers thereof or mixtures thereof; or (ii) the disaccharide comprises sucrose, maltose, cellobiose, gentiobiose, isomaltose, melibiose, primeverose, rutinose, trehalose, lactose or isomers thereof or mixtures thereof.

8. The injectable iron composition of embodiment 6, wherein the starch derivative comprises a dextrin comprising a maltodextrin, a maltose syrup, a glucose syrup or mixtures thereof.

9. The injectable iron composition of embodiment 1, wherein the stabilizing agent comprises an alkalinizing agent, a buffering agent or sucrose.

10. The injectable iron composition of embodiment 1, wherein the iron comprises elemental iron, the carbohydrate comprises sucrose, and the stabilizing agent comprises at least one of a sodium compound, L-histidine, sucrose, or a combination thereof.

11. The injectable iron composition of embodiment 1, wherein the composition has a total volume of (i) not less than 1 mL or (ii) from about 1 mL to about 250 mL or (iii) from about 250 mL to about 500 mL.

12. The injectable iron composition of embodiment 2, wherein (i) the composition comprises elemental iron in an amount of not less than about 1.0 mg/mL; total sucrose in an amount of 95 mg/mL; sodium hydroxide in an amount of 0.96 mg/mL, and optionally L-histidine in an amount of 1.5 mg/mL; (ii) the composition comprises elemental iron in an amount of about 1.0 mg/mL to about 20 mg/mL; (iii) the composition comprises elemental iron in an amount of about 1.0 mg/mL to 2.0 mg/mL, sucrose in an amount of about 15 mg/mL to 195 mg/mL or 15 mg/mL to 115 mg/mL, sodium hydroxide in an amount of about 0.08 mg/mL to 0.96 mg/mL or 0.08 mg/mL to 28.3 mg/mL, and optionally L-histidine in an amount of about 0 mg/mL to about 1.5 mg/mL; or (iv) the composition comprises elemental iron in an amount of about 1.0 mg/mL to 2.0 mg/mL, sucrose in an amount of about 15 mg/mL to 195 mg/mL or 15 mg/mL to 115 mg/mL per 1 mg or 2 mg of iron, sodium hydroxide in an amount of about 0.08 mg/mL to 0.96 mg/mL or 0.08 mg/mL to 28.3 mg/mL per 1 mg or 2 mg of iron, and optionally L-histidine in an amount of about 0 mg/mL to about 1.5 mg/mL per 1 mg or 2 mg of iron.

13. The injectable iron composition of embodiment 9, wherein the alkalinizing agent comprises sodium hydroxide, potassium hydroxide, calcium hydroxide or a combination thereof.

14. The injectable iron composition of embodiment 9, wherein the buffering agent comprises sodium carbonate, sodium bicarbonate, potassium carbonate, potassium bicarbonate, calcium carbonate, calcium bicarbonate or a mixture thereof.

15. The injectable iron composition of embodiment 9, wherein the buffering agent comprises L-histidine, glycine, arginine, tyrosine, lysine or a mixture thereof.

16. The injectable iron composition of embodiment 10, wherein the sodium compound is sodium hydroxide, sodium chloride, sodium gluconate or a combination thereof.

17. The injectable iron composition of embodiment 4, wherein the elemental iron in the colloidal iron (III) carbohydrate complex is from about 1 mg/mL to about 2 mg/mL, and the injectable iron composition comprises a total sucrose in an amount from about 5 to about 195 mg/mL, sodium hydroxide in an amount from about 0.08 to about 28.3 mg/mL and L-histidine in an amount from about 0 to about 1.5 mg/mL.

18. The injectable iron composition of embodiment 4, wherein the iron (III) carbohydrate complex comprises iron sucrose, the iron sucrose comprising elemental iron (III) from about 1 mg/mL to about 2 mg/mL and sucrose from about 15 to about 30 mg/mL, and the injectable iron composition comprises a stabilizing agent comprising sodium hydroxide from about 0.07 to about 0.97 mg/mL, L-histidine from about 0 to about 1.5 mg/mL and a total sucrose from about 15 to about 195 mg/mL.

19. The injectable iron composition of embodiment 16, wherein the elemental iron is 1 mg/mL, a total sucrose from about 57.5 to about 95 mg/mL, sodium hydroxide from about 0.07 to about 0.97 mg/mL and L-histidine from about 0 to about 1.5 mg/mL.

20. The injectable iron composition of embodiment 10, wherein sucrose is in an amount greater than 15 mg/mL.

21. The injectable iron composition of embodiment 4, wherein the injectable iron composition has one or more of the following features (i) to (viii): (i) a pH from about 10 to about 11.1; (ii) an average molecular weight (Mw) of the colloidal iron (III) carbohydrate complex from about 34 kDa to about 60 kDa; (iii) a number average molecular weight (Mn) of the colloidal iron (III) carbohydrate complex from about 24 kDa to about 60 kDa; (iv) a polydispersity index of the colloidal iron (III) carbohydrate complex from about 1.0 to about 1.7; (v) an amount of elemental Fe(II) in the composition from about 0.01% to about 0.04%; (vi) an amount of elemental Fe(II) in the composition from about 0.01% to not more than 0.4%; (vii) a time required for 75% of elemental trivalent iron to be released from the iron composition from about not more than 20 minutes; or (viii) a storage stability of about 24 months.

22. The injectable iron composition of embodiment 4, wherein (i) the iron (III) carbohydrate complex comprises an iron monosaccharide complex, an iron disaccharide complex, an iron oligosaccharide complex, an iron polysaccharide complex or combinations thereof; or (ii) wherein the iron polysaccharide complex comprises iron carboxymaltose, iron sucrose, iron polyisomaltose, iron polymaltose, iron gluconate, iron sorbitol, iron hydrogenated dextran, iron derisomaltose or mixtures thereof.

23. The injectable iron composition of embodiment 21, wherein the injectable iron composition is at least one of a preservative-free composition, a sterile composition, or a ready-to-use injectable aqueous composition.

24. The injectable iron composition of embodiment 1, wherein (i) the injectable iron composition is disposed in a container; (ii) the injectable iron composition is heated from about 60° C. to about 132° C.; or (iii) the injectable iron composition is kept at room temperature.

25. The injectable iron composition of embodiment 24, wherein the container comprises a single use vial or ampule or a bag or the container comprises a vial having a barrier coated stopper and/or an aluminum cap.

26. The injectable iron composition of embodiment 25, wherein (i) the vial or ampule comprises glass or plastic material; (ii) the bag comprises plastic material; (iii) the vial or ampule comprises coated glass; or (iv) the injectable iron composition is in container, which is a syringe.

27. The injectable iron composition of embodiment 24, wherein the container has a headspace oxygen comprising (i) from 0.5% v/v to 5.0% v/v from the time of manufacture to about 6 months from manufacture when stored at temperatures from 25° C. to 60° C.; (ii) from 0.5% v/v to 10.0% v/v from the time of manufacture to about 6 months from manufacture when stored at temperatures from 25° C. to 60° C.; or (iii) from about atmospheric to about 9 mg/L and dissolved oxygen present in the composition in an amount from about 0.1 parts per million (ppm) to about 9 ppm from the time of manufacture to about 1 month from manufacture when stored at room temperature, and the composition is enclosed in a single-use container having a volume of (a) from not less than 1 mL to about 10 mL; or (b) from about 10 mL to about 250 mL.

28. A method of making a stable injectable iron composition, the method comprising (i) mixing an iron and/or a colloidal iron (III) carbohydrate complex with a carbohydrate and water to form a mixture, adding a stabilizing agent to the mixture to form the stable injectable iron composition or (ii) mixing a colloidal iron (III) carbohydrate complex with a carbohydrate and water to form a mixture, adding a stabilizing agent to the mixture to form the stable injectable iron composition.

29. The method of making of embodiment 28, wherein the carbohydrate comprises a monosaccharide, a disaccharide, an oligosaccharide or a polysaccharide.

30. The method of embodiment 28, wherein the iron is elemental iron, the elemental iron and the carbohydrate form a colloidal iron (III) carbohydrate complex.

31. The method of embodiment 28, wherein the colloidal iron (III) carbohydrate complex comprises iron carboxymaltose, iron sucrose, iron polyisomaltose, iron polymaltose, iron gluconate, iron sorbitol, iron hydrogenated dextran, iron derisomaltose, derived carbohydrate-coated, superparamagnetic iron oxide or mixtures thereof.

32. The method of embodiment 28, wherein the stabilizing agent comprises an alkalinizing agent, a buffering agent, sucrose or a mixture thereof.

33. The method of embodiment 28, wherein the iron comprises elemental iron, the carbohydrate comprises sucrose, and the stabilizing agent comprises at least one of sodium, L-histidine, or sucrose.

34. The method of embodiment 28, further comprising adding the composition to a container.

35. The method of embodiment 28, further comprising filtering the composition.

36. The method of embodiment 34, further comprising sterilizing the composition by terminal sterilization or autoclave.

37. The method of embodiment 28, wherein the composition has a pH from about 10 to about 11.5.

38. The method of embodiment 34, wherein the container comprises a single use vial or ampule or a bag or the container comprises a vial having a barrier coated stopper and/or an aluminum cap.

39. The method of embodiment 38, wherein (i) the vial or ampule comprises glass or plastic material or (ii) the bag comprises plastic material.

40. The method of embodiment 38, wherein the container has a headspace oxygen comprising (i) from 0.5% v/v to 5.0% v/v from the time of manufacture to about 6 months from manufacture when stored at temperatures from 25° C. to 60° C.; (ii) from 0.5% v/v to 10.0% v/v from the time of manufacture to about 6 months from manufacture when stored at temperatures from 25° C. to 60° C.; or (iii) from about atmospheric to about 9 mg/L and dissolved oxygen present in the composition in an amount from about 0.1 parts per million (ppm) to about 9 ppm from the time of manufacture to about 1 month from manufacture when stored at room temperature, and the composition is enclosed in a single-use container having a volume of (a) from not less than 1 mL to about 10 mL; or (b) from about 10 mL to about 250 mL.

41. A method of treating a disease, disorder, or condition characterized by iron deficiency or dysfunctional iron metabolism, the method comprising administering to a subject in need of treatment a stable injectable iron composition comprising iron, a carbohydrate, a stabilizing agent and water.

42. The method of embodiment 41, wherein the composition is administered intravenously.

43. The method of embodiment 41, wherein the composition is administered by intravenous push over (i) from about 1 minute to about 15 minutes or (ii) from 1 minute to about 150 minutes.

44. The method of embodiment 41, wherein the stable injectable iron composition is administered in a single dosage unit of at least 1 mg/mL of elemental iron.

45. The method of embodiment 44, wherein the dosage unit does not require dilution before use.

46. The method of embodiment 44, wherein the single dosage unit of at least 1 mg/mL of elemental iron is administered in less than 25 minutes, less than 10 minutes, or less than 5 minutes or less than 1 minute.

47. The method of embodiment 41, wherein (i) the disease, disorder, or condition is anemia; (ii) the disease disorder or condition is iron deficiency anemia; or (iii) the disease disorder or condition is iron deficiency anemia associated with chronic blood loss; acute blood loss; pregnancy; childbirth; childhood development; psychomotor and cognitive development in children; breath holding spells; heavy uterine bleeding; menstruation; chronic recurrent hemoptysis; idiopathic pulmonary siderosis; chronic internal bleeding; gastrointestinal bleeding; parasitic infections; chronic kidney disease; dialysis; surgery or acute trauma; and chronic ingestion of alcohol, chronic ingestion of salicylates, chronic ingestion of steroids; chronic ingestion of non-steroidal anti-inflammatory agents, or chronic ingestion of erythropoiesis stimulating agents.

48. The method of embodiment 41, wherein (i) the disease disorder or condition is anemia of a chronic disease; (ii) the disease disorder or condition is a chronic disease comprising rheumatoid arthritis; cancer; Hodgkin's leukemia; non-Hodgkin's leukemia; anemia from chemotherapy; inflammatory bowel disease; ulcerative colitis; thyroiditis; hepatitis; systemic lupus erythematosus; polymyalgia rheumatica; scleroderma; mixed connective tissue disease; Sjogren's syndrome; congestive heart failure/cardiomyopathy; or (iii) idiopathic geriatric anemia.

49. The method of embodiment 47, wherein (i) the anemia is due to impaired iron absorption or poor nutrition; or (ii) the anemia is associated with Crohn's Disease; gastric surgery; ingestion of drug products that inhibit iron absorption; and chronic use of calcium.

50. The method of embodiment 41, wherein the disease, disorder, or condition comprises blood donation, Parkinson's disease, hair loss, restless leg syndrome or attention deficit disorder.

51. The method of embodiment 41, wherein the iron is elemental iron.

52. The method of embodiment 41, wherein the carbohydrate comprises a monosaccharide, a disaccharide, an oligosaccharide or a polysaccharide.

53. The method of embodiment 51, wherein the elemental iron and the carbohydrate form a colloidal iron (III) carbohydrate complex.

54. The method of embodiment 41, wherein the composition comprises iron carboxymaltose, iron sucrose, iron polyisomaltose, iron polymaltose, iron gluconate, iron sorbitol, iron hydrogenated dextran, iron derisomaltose, derived carbohydrate-coated, superparamagnetic iron oxide, or mixtures thereof.

55. The method of embodiment 52, wherein (i) the monosaccharide comprises glucose, galactose, fructose or mixtures thereof; (ii) the disaccharide comprises sucrose, lactose, maltose, or mixtures thereof; (iii) the oligosaccharide comprises raffinose, stachyose, verbascose or mixtures thereof; or (iv) the polysaccharides comprise starch, a starch derivative, dextran, cellulose, glycogen or mixtures thereof.

56. The method of embodiment 52, wherein (i) the monosaccharide comprises dihydroxyacetone, glyceraldehyde, erythrose, ribose, ribulose, sorbose, xylose, arabinose, fructose, glucose, galactose, mannose, or mixtures thereof; or (ii) the disaccharide comprises sucrose, maltose, cellobiose, gentiobiose, isomaltose, melibiose, primeverose, rutinose, trehalose, lactose or mixtures thereof.

57. The method of embodiment 55, wherein the starch derivative comprises a dextrin comprising a maltodextrin, a maltose syrup or a glucose syrup.

58. The method of embodiment 41, wherein the stabilizing agent comprises an alkalinizing agent, a buffering agent, sucrose, or a mixture thereof.

59. The method of embodiment 41, wherein the iron comprises elemental iron, the carbohydrate comprises sucrose, and the stabilizing agent comprises at least one of a sodium compound, L-histidine, sucrose or a combination thereof.

60. The method of embodiment 41, wherein the composition has a total volume of (i) not less than 1 mL or (ii) from 1 mL to about 10 mL; or (iii) from about 10 mL to about 250 mL.

61. The method of embodiment 58, wherein the composition comprises elemental iron in an amount of 1.0 mg, total sucrose in an amount of about 95 mg, sodium hydroxide in an amount of about 0.08 mg, and optionally L-histidine in an amount of about 0.75 mg/mL.

62. The method of embodiment 58, wherein the alkalinizing agent comprises sodium hydroxide, potassium hydroxide, calcium hydroxide or a combination thereof.

63. The method of embodiment 58, wherein the buffering agent comprises sodium carbonate, sodium bicarbonate, potassium carbonate, potassium bicarbonate, calcium carbonate, calcium bicarbonate or a mixture thereof.

64. The method of embodiment 58, wherein the buffering agent comprises L-histidine, glycine, arginine, tyrosine or lysine.

65. The method of embodiment 59, wherein the sodium compound is sodium hydroxide or sodium chloride.

66. The method of embodiment 59, wherein the elemental iron in the colloidal iron carbohydrate complex is from about 1 mg/mL to about 2 mg/mL, the sucrose is from about 5 to about 195 mg/mL, sodium hydroxide is from about 0.07 to about 28.3 mg/mL or to about 0.96 mg/mL and L-histidine from about 0 to about 0.9 mg/mL.

67. The method of embodiment 65, wherein the colloidal iron carbohydrate complex comprises iron sucrose, the composition comprises elemental iron (III) from about 1 mg/mL to about 2 mg/mL and the iron sucrose comprises sucrose in an amount from about 15 to about 30 mg/mL, and the composition comprises sodium hydroxide from about 0.08 to about 28.3 mg/mL, L-histidine from about 0 to about 0.9 mg/mL and the composition has a total sucrose content from about 15 to about 195 mg/mL.

68. The method of embodiment 65, wherein the content of iron in the composition is 1 mg/mL, the total content of sucrose in the composition is from about 57.5 to about 95 mg/mL, content of sodium hydroxide in the composition is from about 0.08 to about 0.08 mg/mL and the content of L-histidine in the composition from about 0 to about 0.75 mg/mL.

69. The method of embodiment 59, wherein amount of sucrose in the composition is greater than 15 mg/mL.

70. The method of embodiment 53, wherein the composition has one or more of the following features (i) to (viii): (i) a pH from about 10 to about 11.1; (ii) an average molecular weight (Mw) of the colloidal iron (III) carbohydrate complex from about 34 kDa to about 60 kDa; (iii) a number average molecular weight (Mn) of the colloidal iron (III) carbohydrate complex from about 24 kDa to about 60 kDa; (iv) a polydispersity index of the colloidal iron (III) carbohydrate complex from about 1.0 to about 1.7; (v) an amount of elemental Fe(II) in the composition from about 0.01% to about 0.04%; (vi) an amount of elemental Fe(II) in the composition from about 0.01% to not more than 0.4%; (vii) a time required for 75% of elemental trivalent iron to be released from the iron composition from about not more than 20 minutes; or (viii) a storage stability of about 24 months.

71. The method of embodiment 53, wherein (i) the iron (III) carbohydrate complex comprises an iron monosaccharide complex, an iron disaccharide complex, an iron oligosaccharide complex, an iron polysaccharide complex or combinations thereof; or (ii) the iron polysaccharide complex comprises iron carboxymaltose, iron sucrose, iron polyisomaltose, iron polymaltose, iron gluconate, iron sorbitol, iron hydrogenated dextran, iron derisomaltose or mixtures thereof.

72. The method of embodiment 41, wherein the composition is at least one of a preservative-free composition, a sterile composition, or a ready-to-use injectable aqueous composition.

73. The method of embodiment 41, wherein the composition is disposed in a container.

74. The method of embodiment 73, wherein the container comprises a single use vial or ampule or a bag or the container comprises a vial having a barrier coated stopper and/or an aluminum cap.

75. The method of embodiment 74, wherein the vial, ampule or bag comprising of glass or plastic material.

76. The method of embodiment 75, wherein the container has a headspace oxygen comprising (i) from 0.5% v/v to 5.0% v/v from the time of manufacture to about 6 months from manufacture when stored at temperatures from 25° C. to 60° C.; (ii) from 0.5% v/v to 10.0% v/v from the time of manufacture to about 6 months from manufacture when stored at temperatures from 25° C. to 60° C.; or (iii) from about atmospheric to about 9 mg/L and dissolved oxygen present in the composition in an amount from about 0.1 parts per million (ppm) to about 9 ppm from the time of manufacture to about 1 month from manufacture when stored at room temperature, and the composition is enclosed in a single-use container having a volume of (a) from not less than 1 mL to about 10 mL; or (b) from about 10 mL to about 250 mL.

77. The composition of any one of embodiments 1-27, wherein the composition is administered to a human.

78. The method of any one of embodiments 28-76, wherein the composition is administered to a human.

79. An injectable iron composition comprising a colloidal iron-carbohydrate complex, a stabilizing agent and water.

80. The injectable iron composition of embodiment 79, wherein the carbohydrate is a sugar comprising glucose and fructose.

81. The injectable iron composition of embodiment 4, wherein the colloidal iron-carbohydrate complex comprises iron sucrose, wherein the weight ratio of elemental iron (III) to (i) sucrose is from about 1:15 to about 1:200; (ii) Na+ ion is from about 1:0.04 to about 1:28.5 and/or (iii) L-histidine is from about 1:0 to about 1:1.5.

82. The injectable iron composition of embodiment 4, wherein the colloidal iron-carbohydrate complex comprises iron sucrose, wherein the molar ratio of elemental iron (III) to (i) sucrose is from about 1:2.4 to about 1:32; (ii) Na+ ion is from about 1:0.05 to about 1:39.3 or (iii) L-histidine is from about 1:0 to about 1:0.55.

83. The injectable iron composition of any one of embodiments 1-27, wherein the injectable iron composition maintains a density of about 1.027 to about 1.047 g/mL or about 1.037 to about 1.058 g/mL for a period of up to 24 months.

84. The injectable iron composition of any one of embodiments 4-27, wherein the colloidal iron (III) carbohydrate complex has an average molecular weight (Mw) from about 34 kDa to about 60 kDa for a period of up to 24 months.

85. The injectable iron composition of any one of embodiments 4-27, wherein the colloidal iron (III) carbohydrate complex has a number average molecular weight (Mn) from about 24 kDa to about 60 kDa for a period of up to 24 months.

86. The injectable iron composition of any one of embodiments 4-27, wherein the colloidal iron (III) carbohydrate complex has a polydispersity index from about 1.0 to about 1.7 for a period of up to 24 months.

87. The injectable iron composition of embodiment 2, wherein (i) the injectable iron composition comprises elemental iron in an amount of not less than 1.0 mg/mL to 2.0 mg/mL, total sucrose in an amount of about 5 mg/mL to about 160 mg/mL, sodium hydroxide in an amount of about 0.08 mg/mL to about 0.96 mg/mL, and optionally L-histidine in an amount of about 0.75 mg/mL to about 1.5 mg/mL.

88. An injectable iron composition comprising an iron (III)-hydroxide-sucrose complex comprising 1 mg/mL to 2 mg/mL of elemental iron; sucrose in an amount greater than 15 mg/mL of the injectable iron composition, a sodium compound comprising sodium acetate, sodium hydroxide, sodium carbonate, sodium bicarbonate or mixtures thereof; and water.

89. The injectable iron composition of embodiment 88, wherein the iron (III)-hydroxide-sucrose complex comprises 1 mg/mL-15 mg/mL of sucrose complexed with the iron (III)-hydroxide.

90. The injectable iron composition of embodiment 89, wherein the injectable iron composition comprises from about 1 mg/mL-185 mg/mL of sucrose that is added to the iron (III)-hydroxide-sucrose complex.

91. The injectable iron composition of embodiment 89, wherein the sodium compound comprises sodium hydroxide in an amount from about 0.08 mg/mL to about 28.3 mg/mL of the injectable iron composition.

92. The injectable iron composition of embodiment 89 further comprising L-histidine in an amount from about 0.01 mg/mL to about 1.5 mg/mL of the injectable iron composition.

93. The injectable iron composition of embodiment 89, wherein the injectable iron composition has a pH of about 9.6 to about 11.4.

94. The injectable iron composition of any one of embodiments 88-93, wherein the injectable iron composition provides about 1 mg/mL to about 2 mg/mL of elemental iron.

95. An injectable iron composition comprising an iron (III)-hydroxide-sucrose complex comprising about 1 mg/mL of elemental iron bound to about 15 mg/mL of sucrose; a stabilizing agent comprising about 80 mg/mL of sucrose and about 0.08 mg/mL of sodium hydroxide; and water.

96. An injectable iron composition comprising an iron (III)-hydroxide-sucrose complex comprising about 2 mg/mL of elemental iron bound to about 30 mg/mL of sucrose; a stabilizing agent comprising about 85 mg/mL of sucrose and about 0.96 mg/mL of sodium hydroxide; and water.

97. An injectable iron composition comprising an iron (III)-hydroxide-sucrose complex comprising about 1 mg/mL of iron; about 95 mg/mL of sucrose; about 0.08 mg/mL of sodium hydroxide; and water.

98. An injectable iron composition comprising an iron (III)-hydroxide-sucrose complex comprising about 2 mg/mL of iron; about 115 mg/mL of sucrose; about 0.96 mg/mL of sodium hydroxide; and water.

99. The injectable iron composition of any one of embodiments 95-98, wherein the injectable iron composition has a pH of about 9.6 to about 11.4.

100. The injectable iron composition of any one of embodiments 95-99, wherein the injectable iron composition provides about 1 mg/mL to about 2 mg/mL of elemental iron.

101. The injectable iron composition of any one of embodiments 95-100, wherein the injectable iron composition is enclosed in a single-use container and the injectable iron composition has a volume of 100 mL.

102. The injectable iron composition of any one of embodiments 95-101 useful for treating a disease, disorder, or condition characterized by iron deficiency or dysfunctional iron metabolism.

103. A method of making a stable injectable iron composition, the method comprising mixing an iron (III)-hydroxide-sucrose complex comprising about 1 mg/mL of iron bound to about 15 mg/mL of sucrose with a stabilizing agent comprising about 80 mg/mL of sucrose and about 0.08 mg/mL of sodium hydroxide and water to form the stable injectable iron composition.

104. A method of making a stable injectable iron composition, the method comprising mixing an iron (III)-hydroxide-sucrose complex comprising about 2 mg/mL of iron bound to about 30 mg/mL of sucrose with a stabilizing agent comprising about 85 mg/mL of sucrose and about 0.96 mg/mL of sodium hydroxide and water to form the stable injectable iron composition.

105. A method of making a stable injectable iron composition, the method comprising mixing an iron (III)-hydroxide-sucrose complex comprising about 1 mg/mL of iron with about 95 mg/mL of sucrose and about 0.08 mg/mL of sodium hydroxide and water to form the stable injectable iron composition.

106. A method of making a stable injectable iron composition, the method comprising mixing an iron (III)-hydroxide-sucrose complex comprising about 2 mg/mL of iron with about 115 mg/mL of sucrose and about 0.96 mg/mL of sodium hydroxide and water to form the stable injectable iron composition.

107. The method of any one of embodiments 103-106, wherein the stable injectable iron composition has a pH of about 9.6 to about 11.4.

108. The method of any one of embodiments 103-107, wherein the injectable iron composition provides about 1 mg/mL to about 2 mg/mL of elemental iron.

109. The method of any one of embodiments 103-108, further comprising enclosing the stable injectable iron composition in a single-use container and the injectable iron composition has a volume of 100 mL.

110. An injectable iron composition comprising an iron (III)-hydroxide-sucrose complex comprising 1 mg/mL to about 2 mg/mL of iron, additional sucrose apart from the sucrose of the iron (III)-hydroxide-sucrose complex, a stabilizing agent and water.

111. An injectable iron composition comprising an iron (III)-hydroxide-sucrose complex comprising about 1 mg/mL of iron; a stabilizing agent comprising about 80 mg of sucrose per 1 mg of iron and about 0.08 mg of sodium hydroxide per 1 mg of iron; and water.

112. An injectable iron composition comprising an iron (III)-hydroxide-sucrose complex comprising about 2 mg/mL of iron; a stabilizing agent comprising about 85 mg of sucrose per 2 mg of iron and about 0.96 mg of sodium hydroxide per 2 mg of iron; and water.

113. An injectable iron composition comprising an iron (III)-hydroxide-sucrose complex comprising about 1 mg/mL of iron; about 95 mg of sucrose per 1 mg of iron; about 0.08 mg of sodium hydroxide per 1 mg of iron; and water.

114. An injectable iron composition comprising an iron (III)-hydroxide-sucrose complex comprising about 2 mg/mL of iron; about 115 mg of sucrose per 2 mg of iron; about 0.96 mg of sodium hydroxide per 2 mg of iron; and water.

115. An injectable iron composition comprising iron in an amount of not less than 1.0 mg/mL to 2.0 mg/mL, total sucrose in an amount of about 5 mg to about 160 mg per 1 mg or 2 mg of iron, sodium hydroxide in an amount of about 0.08 mg to about 0.96 mg per 1 mg or 2 mg of iron, and optionally L-histidine in an amount of about 0.75 mg to about 1.5 mg per 1 mg or 2 mg of iron.

116. The injectable iron composition of embodiment 110, wherein the additional sucrose apart from the sucrose of the iron (III)-hydroxide-sucrose complex comprises at least about 5 mg to about 185 mg per 1 mg or 2 mg of iron, sodium hydroxide in an amount of about 0.08 mg to about 28.3 mg per 1 mg or 2 mg of iron, and optionally L-histidine in an amount of about 0.75 mg to about 1.5 mg per 1 mg or 2 mg of iron.

117. The injectable iron composition of any one of embodiments 111-116, wherein the injectable iron composition has a pH of about 9.6 to about 11.4.

118. The injectable iron composition of any one of embodiments 111-117, wherein the injectable iron composition provides about 1 mg/mL to about 2 mg/mL of elemental iron.

119. The injectable iron composition of any one of embodiments 1-27, 79-102, or 110-118, wherein the injectable iron composition has the pH adjusted using an acid.

120. The method of any one of embodiments 28-40, or 103-109, wherein the injectable iron composition has the pH adjusted using an acid.

EXAMPLES

Examples 1, 2, 3, 4, and 5

Examples of the stable, ready-to-use injectable iron sucrose compositions containing 1 mg/mL of elemental iron are described below in Examples 1-4. Example 5 being a comparative example illustrating a Venofer® intravenous admixture is also included.

In Examples 1, 2, 3, and 4, each mL of the formulation comprises:

| Example 1: Batch 3RJ191025-1 | |
|---|---|
| Elemental Iron | 1.0 mg/mL |
| Total Sucrose** | 57.5 mg/mL |
| Na Ion (NaOH) | 2 mM (0.08 mg/mL) |
| L-Histidine | 0.75 mg/mL |
| Water for Injection | Q.S. to 1 mL |

| Example 2: Batch 3RJ191025-6 | |
|---|---|
| Elemental Iron | 1.0 mg/mL |
| Total Sucrose** | 95.0 mg/mL |
| Na Ion (NaOH) | 2 mM (0.08 mg/mL) |
| L-Histidine | 1.5 mg/mL |
| Water for Injection | Q.S. to 1 mL |

| Example 3: Batch 3RJ191025-12 | |
|---|---|
| Elemental Iron | 1.0 mg/mL |
| Total Sucrose** | 95 mg/mL |
| Na Ion (NaOH) | 2 mM (0.08 mg/mL) |
| Water for Injection | Q.S. to 1 mL |

| Example 4: Batch 3RJ191025-14 | |
|---|---|
| Elemental Iron | 1.0 mg/mL |
| Total Sucrose** | 95 mg/mL |
| Na Ion (NaOH) | 24 mM (0.96 mg/mL) |
| L-Histidine | 0.75 mg/mL |
| Water for Injection | Q.S. to 1 mL |

** 1 mg of iron is provided as an iron-sucrose complex containing about 15 mg of sucrose. Total sucrose includes the amount of added sucrose, NF and the amount already complexed with the elemental iron.

In some embodiments, the iron sucrose compositions (Examples 1-4) can be heated, for example, at about 60° C. to about 132° C. after placement in the container (e.g., vials) or be kept at room temperature.

Venofer® Intravenous Admixture diluted with 0.9% NaCl (1 mg/mL, elemental iron) was prepared as a control solution to evaluate the efficacy of the selected excipients to stabilize the formulation. The control Venofer® composition is summarized below:

| Example 5 Comparative Example 3RJ190618-5 | |
|---|---|
| Elemental Iron | 1.0 mg/mL |
| Sucrose | 15 mg/mL |

-continued

| Example 5 Comparative Example 3RJ190618-5 | |
|---|---|
| NaCl (Na Ion) | 9 mg/mL (154 mM) |
| Water for Injection | Q.S. to 1 mL |

Iron compositions were prepared using the same compounding process and filled into the same container closure system (5 mL molded Type I glass vials with 13 mm Teflon rubber stoppers and aluminum cap/flip-off seals) under ambient conditions before evaluating the stability of each composition. The only difference between the iron compositions of Examples 1 to 4 and the formulation of the comparative example was the presence and concentration of the included stabilizing excipients, sucrose, NaOH and L-Histidine. For example, Example 3 illustrates an iron composition having an increased amount of sucrose by comparison to Venofer® IV admixture of Example 5. The stability of the compositions in Examples 1, 2, 3, and 4, was assessed by monitoring parameters such as Mw, Mn, PDI, pH, appearance, Iron (II) content as an impurity, and controlled release test for trivalent iron (T75) for demonstration of equivalency when compared with Venofer® a currently approved formulation. The results of the compositions of Examples 1, 2, 3, 4, and comparative Example 5, are summarized below in Tables I, II and III.

TABLE I

| Condition: 25 ± 2° C./60 ± 5% RH[1] | | | | | | | | |
|---|---|---|---|---|---|---|---|---|
| Parameter (Specification) | | pH | | Mw (34,000-60,000 Da) | | Mn (≥24,000 Da) | | PDI (≤1.7) |
| Time (Month) | | T0 | T3 | T0 | T3 | T0 | T3 | T0 | T3 |
| Example 1 | 3RJ191025-1 | 11.0 | 10.6 | 52,657 | 52,169 | 37,259 | 35,690 | 1.41 | 1.46 |
| Example 2 | 3RJ191025-6 | 11.0 | 10.8 | 58,983 | 52,817 | 42,846 | 35,911 | 1.38 | 1.47 |
| Example 3 | 3RJ191213-12 | 11.1 | 10.9 | 53,046 | 52,641 | 38,036 | 35,931 | 1.39 | 1.47 |
| Example 4 | 3RJ191217-14 | 11.1 | 11.0 | 54,191 | 53,663 | 38,195 | 36,755 | 1.42 | 1.46 |
| Example 5 | 3RJ190618-5 | 10.14 | 9.80 | 55,931 | 101,192 | 38,907 | 55,052 | 1.44 | 1.84 |

[1]ICH Q1A(R2) Stability Testing of New Drug Substances and Products

TABLE II

| Condition: 30 ± 2° C./65 ± 5% RH[1] | | | | | | | | | | | | | |
|---|---|---|---|---|---|---|---|---|---|---|---|---|---|
| Parameter (Specification) | | pH(TBD) | | | | | | Mw(4000-60000 Da) | | | | | |
| Time (Month) | | T0 | T1 | T3 | T4 | T5 | T6 | T0 | T1 | T3 | T4 | T5 | T6 |
| Example1 | 3RJ1910251 | 11.0 | 10.6 | 10.6 | 10.5 | 10.5 | 10.4 | 52,657 | 52,372 | 51,195 | 53,573 | 55,415 | 53,070 |
| Example2 | 3RJ1910256 | 11.0 | 10.8 | 10.8 | 10.8 | 10.7 | 10.7 | 58,983 | 51,840 | 49,026 | 53,399 | 55,788 | 52,716 |
| Example3 | 3RJ191213-12 | 11.1 | 10.8 | 10.8 | 10.8 | 10.8 | 10.7 | 53,046 | 50,870 | 49,494 | 53,281 | 56,628 | 52,698 |
| Example4 | 3RJ191217-14 | 11.1 | 10.9 | 11.0 | 11.0 | 10.9 | 10.9 | 54,191 | 51,452 | 49,863 | 53,342 | 57,039 | 52,781 |

| Parameter (Specification) | | Mn(≥24,000 Da) | | | | | | PDI(≤1.7) | | | | | |
|---|---|---|---|---|---|---|---|---|---|---|---|---|---|
| Time (Month) | | T0 | T1 | T3 | T4 | T5 | T6 | T0 | T1 | T3 | T4 | T5 | T6 |
| Example1 | 3RJ1910251 | 37,259 | 37,242 | 34,941 | 38,598 | 38,605 | 38,960 | 1.41 | 1.41 | 1.47 | 1.39 | 1.44 | 1.4 |
| Example2 | 3RJ1910256 | 42,846 | 36,662 | 33,047 | 38,386 | 38,904 | 38,370 | 1.38 | 1.41 | 1.48 | 1.39 | 1.43 | 1.4 |
| Example3 | 3RJ191213-12 | 38,036 | 35,911 | 33,351 | 38,353 | 39,594 | 38,433 | 1.39 | 1.42 | 1.48 | 1.39 | 1.43 | 1.4 |
| Example4 | 3RJ191217-14 | 38,195 | 36,365 | 33,610 | 38,303 | 39,392 | 38,397 | 1.42 | 1.41 | 1.48 | 1.39 | 1.43 | 1.4 |

[1]ICH Q1A(R2) Stability Testing of New Drug Substances and Products

TABLE III

| Condition: 40 ± 2° C./75 ± 5% RH[1] | | | | | | | | | | | | | |
|---|---|---|---|---|---|---|---|---|---|---|---|---|---|
| Parameter (Specification) | | pH (TBD) | | | | | | Mw (4000-60,000 Da) | | | | | |
| Time (Month) | | T0 | T1 | T3 | T4 | T5 | T6 | T0 | T1 | T3 | T4 | T5 | T6 |
| Example1 | 3RJ191025-1 | 11.0 | 10.5 | 10.7 | 10.3 | 10.3 | 10.1 | 52,657 | 52,510 | 58,002 | 55,115 | 58,598 | 55,624 |
| Example2 | 3RJ191025-6 | 11.0 | 10.7 | 10.7 | 10.6 | 10.6 | 10.5 | 58,983 | 52,554 | 57,236 | 53,977 | 57,464 | 53,995 |
| Example3 | 3RJ191213-12 | 11.1 | 10.7 | 10.7 | 10.6 | 10.5 | 10.4 | 53,046 | 51,180 | 58,150 | 53,529 | 56,925 | 52,620 |

TABLE III-continued

| | | Condition: 40 ± 2° C./75 ± 5% RH[1] | | | | | | | | | | |
|---|---|---|---|---|---|---|---|---|---|---|---|---|
| Example4 | 3RJ191217-14 | 11.1 | 10.8 | 10.9 | 10.8 | 10.8 | 10.7 | 54,191 | 51,329 | 59,635 | 51,492 | 59,362 | 55,169 |
| Example5 | 3RJ190618-5 | 10.14 | 95.3 | | NT | | | 55,931 | 120,628 | 745,168 | | NT | |

| Parameter (Specification) | | Mn (≥24,000 Da) | | | | | | PDI (≤1.7) | | | | | |
|---|---|---|---|---|---|---|---|---|---|---|---|---|---|
| Time (Month) | | T0 | T1 | T3 | T4 | T5 | T6 | T0 | T1 | T3 | T4 | T5 | T6 |
| Example1 | 3RJ191025-1 | 37,259 | 37,514 | 40,761 | 40,009 | 41,209 | 41,039 | 1.41 | 1.40 | 1.42 | 1.38 | 1.42 | 1.4 |
| Example2 | 3RJ191025-6 | 42,846 | 37,389 | 39,777 | 38,948 | 40,286 | 39,342 | 1.38 | 1.41 | 1.44 | 1.39 | 1.43 | 1.4 |
| Example3 | 3RJ191213-12 | 38,036 | 36,242 | 40,693 | 38,615 | 39,937 | 38,464 | 1.39 | 1.41 | 1.43 | 1.39 | 1.43 | 1.4 |
| Example4 | 3RJ191217-14 | 38,195 | 36,293 | 41,704 | 39,228 | 41,625 | 40,682 | 1.42 | 1.41 | 1.43 | 1.39 | 1.43 | 1.4 |
| Example5 | 3RJ190618-5 | 38,907 | 64,530 | 135,622 | | NT | | 1.44 | 1.87 | 5.50 | | NT | |

[1]ICH Q1A(R2) Stability Testing of New Drug Substances and Products

The stabilized ready-to-use (RTU) iron composition of examples 1, 2, 3, and 4, met the acceptance criteria described in the current USP monograph (Venofer® Iron Sucrose Injection) for Mw, Mn, PDI, limit of iron [Fe(II)], and the absence of low-molecular weight Iron [Fe(II) and Fe(III) complexes] at 25±2° C./60±5% RH (long-term), 30±2° C./65±5% RH (intermediate) and 40±2° C./75±5% (accelerated) storage conditions for up to 6 months. Specifically, the polydispersity of the iron compositions of examples 1, 2, 3, and 4, did not exceed a value of 1.7. Fe(II) content in the iron compositions of examples 1, 2, 3, and 4, did not exceed 0.4%. The control formulation of comparative example 5 (Venofer® Intravenous Admixture) exhibited less desirable values for pH, Mw, and PDI specifications at 25±2° C./60±5% RH (long-term) within 3 months and at 40±2° C./75±5% RH (accelerated) within 1 month.

As can be seen from Table I, II, and III above, the addition of sucrose, NaOH and/or L-Histidine enhanced the storage stability (long-term, intermediate, and accelerated condition) of the iron sucrose compositions. Without being bound by theory, it is believed that the addition of the stabilizing agents of sucrose, a sodium ion, and/or buffer, provided, for example, by sodium hydroxide and/or L-histidine prevents the aggregation of iron sucrose resulting from an increase in the weight average molecular weight, decrease in pH, change in iron species, and precipitation of the iron-sucrose complex.

The ready-to-use (RTU) iron compositions or iron sucrose compositions of Examples 1, 2, 3, and 4, showed greater stability of the iron-sucrose colloid at a concentration of 1 mg/mL elemental iron in comparison to the currently available formulation for IV administration of iron sucrose injection, 20 mg/mL which is to be diluted with 0.9% NaCl for IV infusion at the time of administration. The above admixture stability studies illustrated in Table I, II, and III have demonstrated that the 20 mg/mL iron sucrose injection which when added to IV infusion bags containing 0.9% NaCl at concentrations ranging from 1 mg/mL to 2 mg/mL of elemental iron, is physically and chemically stable for 7 days at controlled room temperature of 20-25° C. (USP Packaging and Storage Requirements) while the iron compositions of this application are chemically stable for longer than 7 days and at least 6 months and in many cases for at least 24 months.

The iron compositions described herein provide an improvement, at least, because the stabilized RTU iron sucrose injection 1 mg/mL composition containing sucrose, NaOH, and/or L-Histidine prevents the destabilization of the iron-sucrose complex and maintains the physiochemical properties of the active, and/or environment at accelerated and long-term storage conditions. This ensures that the bioavailability of the iron composition remains unchanged on administration as monitored by T75 test.

Moreover, the stabilized RTU iron sucrose injection 1 mg/mL composition removes the risk for any errors in dilution and eliminates the preparation step needed to ready other iron sucrose intravenous admixture solutions. This further ensures a reduced total patient time for administration of each IV infusion.

Table IV provides several ready-to-use formulations of the stable iron sucrose IV infusion compositions of this application. These formulations are expressed in mg/mL and also in millimoles in Table IV.

TABLE IV

| | Min-Max value | Current values in Proposed Ready-To-Use (RTU) Iron Sucrose IV Infusion mg/mL(mM) | | | |
|---|---|---|---|---|---|
| | preferable (mM) | Formulation #1 | Formulation #2 | Formulation #3 | Formulation #4 |
| Elemental Iron | 1-2 mg/mL (18 mM-36mM) | 1.0 mg/mL | 1.0 mg/mL | 1.0 mg/mL | 1.0 mg/mL |
| **Total | 15-195 or 15-200 | 57.5 mg/mL | 95.0 mg/mL | 95.0 mg/mL | 95.0 mg/mL |

TABLE IV-continued

| | Min-Max value preferable (mM) | Current values in Proposed Ready-To-Use (RTU) Iron Sucrose IV Infusion mg/mL(mM) | | | |
|---|---|---|---|---|---|
| | | Formulation #1 | Formulation #2 | Formulation #3 | Formulation #4 |
| Sucrose | mg/mL (44 mM-570 mM or 44 mM-585 mM) | (168 mM) | (278 mM) | (278 mM) | (278 mM) |
| Na Ion (NaOH) | 0.08- 28.3 mg/mL (2 mM- 708 mM) | 0.08 mg/mL (2 mM) | 0.08 mg/mL (2 mM) | 0.08 mg/mL (2 mM) | 0.96 mg/mL (24 mM) |
| L-Histidine | 0-1.5 mg/mL (0-10 mM) | 0.75 mg/mL (5 mM) | 1.5 mg/mL (10 mM) | NA | 0.75 mg/mL (5 mM) |

**1 mg of iron is provided as an iron-sucrose complex containing about 15 mg of sucrose. Total sucrose includes the amount of added sucrose and the amount already complexed with the elemental iron.

In some embodiments, the iron sucrose compositions (Formulations 1-4) can be heated, for example, from about 60° C. to about 132° C. after placement in the container (e.g., vials) or be kept at room temperature. It is understood by those skilled in the art that the excipients described herein serve only as non-limiting examples of iron carbohydrate stabilization agents. Such non-limiting agents include carbonate buffers, sugar carbohydrates, sugar-lipids, for example. Moreover, iron sucrose serves as non-limiting examples of an active pharmaceutical ingredient that belongs in the category of iron carbohydrates for parenteral iron therapy.

Example 6

Twenty-one ready-to-use injectable iron sucrose compositions containing 1 mg/mL or 2 mg/mL of elemental iron are described below in Table VI. Their stability 25±2° C./60±5% RH, 30±2° C./60±5% RH, and 40±2° C./60±5% RH at time 0, three months, six months and 18 months are shown in Table VII and Table VIII.

The iron compositions in Table VI can be prepared by adding the desired amount of sucrose to water for injection at 20° C.-25° C. in a tank and mixing the additives to form a mixture. To this mixture, sodium hydroxide and optionally histidine is added and mixed. Iron (1 mg iron complexed with about 15 mg of sucrose or 2 mg iron complexed with about 30 mg of sucrose) is then added to the mixture while mixing and then 40% w/v sodium hydroxide and/or hydrochloric acid, is added to adjust the pH to the range of 9.6-11.1 to form the stable injectable iron composition. Sodium bicarbonate can be added as an excipient if needed to keep the pH in the range of 9.6-11.1. The injectable iron composition formed can then be filtered and/or autoclaved and placed in vial, bottle or bag and sealed.

TAVLE VI

| | Iron Compositions | | | |
|---|---|---|---|---|
| QBD | Iron* (mg/mL) | Sucrose** (mg/mL) | Na Ion (mM) | Histidine (mg/mL) |
| 1 | 1 | 42.5 | 2 | 0.75 |
| 2 | 1 | 42.5 | 46 | 0.75 |
| 3 | 1 | 42.5 | 22.9 | 0.8 |
| 4 | 1 | 5.0 | 2.0 | 0.0 |
| 5 | 1 | 80.0 | 46.0 | 0.0 |
| 6 | 1 | 80 | 2 | 1.5 |
| 7 | 1 | 42.5 | 24.0 | 1.5 |
| 8 | 1 | 5.0 | 46.0 | 1.5 |
| 9 | 1 | 5 | 46 | 0 |
| 10 | 1 | 5 | 2 | 1.5 |
| 11 | 1 | 42.5 | 46 | 0.75 |
| 12 | 1 | 80 | 2 | 0 |
| 13 | 1 | 5 | 24 | 0.75 |
| 14 | 1 | 80 | 24 | 0.75 |
| 15 | 1 | 42.5 | 24 | 0.75 |
| 16 | 1 | 80 | 46 | 1.5 |
| 17 | 1 | 42.5 | 24 | 0 |
| 18 | 2 | 160 | 2 | 0 |
| 19**** | 2 | 85 | 24 | 0 |
| 20 | 2 | 160 | 2 | 0.75 |
| 21 | 1 | 80 | 2 | 0*** |

*1 mg of iron is provided as a complex with about 15 mg of sucrose; 2 mg of iron is provided as a complex with about 30 mg of sucrose
**This amount is the amount of added sucrose
***Sodium Bicarbonate = 1.85 mg/mL was used as excipient
****HCl, NF may beised to adjust the pH as needed.

TABLE VII

| | | | Stability Iron 1 mg/mL Compositions | | | | | | | | | | | |
|---|---|---|---|---|---|---|---|---|---|---|---|---|---|---|
| | | | T0 | | | T = 3M | | | T = 6M | | | T = 18M *P-50 Adjusted | | |
| RTU 1 mg/mL | | | Mw 34,000-60,000 | Mn ≥24,000 | PDI ≤1.7 | | Mw 34,000-60,000 | Mn ≥24,000 | PDI ≤1.7 | | Mw 34,000-60,000 | Mn ≥24,000 | PDI ≤1.7 | | Mw 34,000-60,000 | Mn ≥24,000 | PDI ≤1.7 |
| ID | Temp | pH | | | | pH | | | | pH | | | | pH | | | |
| QBD 1 | 25 C. | 11.0 | 60,165 | 42,452 | 1.42 | NT | NT | NT | NT | NT | NT | NT | NT | 10.3 | 48,855 | 33,047 | 1.5 |
| | 30 C. | | | | | 10.4 | 52,874 | 38,802 | 1.4 | 10.4 | 57,863 | 41,424 | 1.4 | NT | NT | NT | NT |
| | 40 C. | | | | | 10.2 | 55,952 | 41,299 | 1.4 | 10.1 | 66,019 | 47,718 | 1.4 | NT | NT | NT | NT |
| QBD 2 | 25 C. | 11.0 | 65,050 | 45,495 | 1.43 | NT | NT | NT | NT | NT | NT | NT | NT | 10.5 | 60,797 | 37,937 | 1.6 |
| | 30 C. | | | | | NT | NT | NT | NT | NT | NT | NT | NT | NT | NT | NT | NT |
| | 40 C. | | | | | 10.5 | 69,293 | 47,816 | NT | NT | NT | NT | NT | NT | NT | NT | NT |

TABLE VII-continued

Stability Iron 1 mg/mL Compositions

| RTU 1 mg/mL ID | Temp | T0 pH | T0 Mw 34,000-60,000 | T0 Mn ≥24,000 | T0 PDI ≤1.7 | T=3M pH | T=3M Mw 34,000-60,000 | T=3M Mn ≥24,000 | T=3M PDI ≤1.7 | T=6M pH | T=6M Mw 34,000-60,000 | T=6M Mn ≥24,000 | T=6M PDI ≤1.7 | T=18M *P-50 Adjusted pH | Mw 34,000-60,000 | Mn ≥24,000 | PDI ≤1.7 |
|---|---|---|---|---|---|---|---|---|---|---|---|---|---|---|---|---|---|
| QBD 3 | 25 C. | 11.0 | 61,972 | 43,792 | 1.42 | NT | NT | NT | NT | NT | NT | NT | NT | 10.5 | 51,451 | 34,203 | 1.5 |
|  | 30 C. |  |  |  |  | NT | NT | NT | NT | 10.6 | 57,189 | 41,134 | 1.4 | NT | NT | NT | NT |
|  | 40 C. |  |  |  |  | 10.5 | 56,854 | 41,528 | 1.4 | NT | NT | NT | NT | NT | NT | NT | NT |
| QBD 4 | 25 C. | 11.0 | 63,343 | 45,520 | 1.39 | NT | NT | NT | NT | NT | NT | NT | NT | 9.7 | 58,560 | 38,964 | 1.5 |
|  | 30 C. |  |  |  |  | NT | NT | NT | NT | 9.8 | 59,528 | 43,604 | 1.4 | NT | NT | NT | NT |
|  | 40 C. |  |  |  |  | 9.7 | 62,096 | 46,036 | 1.3 | NT | NT | NT | NT | NT | NT | NT | NT |
| QBD 5 | 25 C. | 11.0 | 61,035 | 42,592 | 1.43 | NT | NT | NT | NT | NT | NT | NT | NT | 10.6 | 50,955 | 33,609 | 1.5 |
|  | 30 C. |  |  |  |  | NT | NT | NT | NT | 10.6 | 56,721 | 40,467 | 1.4 | NT | NT | NT | NT |
|  | 40 C. |  |  |  |  | 10.6 | 56,992 | 40,859 | 1.4 | NT | NT | NT | NT | NT | NT | NT | NT |
| QBD 6 | 25 C. | 11.0 | 59,787 | 41,935 | 1.43 | NT | NT | NT | NT | NT | NT | NT | NT | 10.6 | 48,760 | 32,837 | 1.5 |
|  | 30 C. |  |  |  |  | 10.7 | 52,362 | 38,088 | 1.4 | 10.6 | 54,609 | 39,355 | 1.4 | NT | NT | NT | NT |
|  | 40 C. |  |  |  |  | 10.6 | 53,859 | 39,315 | 1.4 | 10.5 | 62,258 | 44,917 | 1.4 | NT | NT | NT | NT |
| QBD 7 | 25 C. | 11.0 | 60,839 | 42,830 | 1.42 | NT | NT | NT | NT | NT | NT | NT | NT | 10.4 | 55,247 | 35,995 | 1.5 |
|  | 30 C. |  |  |  |  | NT | NT | NT | NT | 10.4 | 59,546 | 42,666 | 1.4 | NT | NT | NT | NT |
|  | 40 C. |  |  |  |  | 10.3 | 65,037 | 46,289 | 1.4 | NT | NT | NT | NT | NT | NT | NT | NT |
| QBD 8 | 25 C. | 11.0 | 87,208 | 56,401 | 1.55 | NT | NT | NT | NT | NT | NT | NT | NT | 10.1 | 138,308 | 68,121 | 2.0 |
|  | 30 C. |  |  |  |  | NT | NT | NT | NT | NT | NT | NT | NT | NT | NT | NT | NT |
|  | 40 C. |  |  |  |  | 10.1 | 118,798 | 69,336 | NT | NT | NT | NT | NT | NT | NT | NT | NT |
| QBD 9 | 25 C. | 11.0 | 86,441 | 56,951 | 1.52 | NT | NT | NT | NT | NT | NT | NT | NT | 9.8 | 135,585 | 67,050 | 2.0 |
|  | 30 C. |  |  |  |  | NT | NT | NT | NT | NT | NT | NT | NT | NT | NT | NT | NT |
|  | 40 C. |  |  |  |  | 9.9 | 112,529 | 67,088 | NT | NT | NT | NT | NT | NT | NT | NT | NT |
| QBD 10 | 25 C. | 11.0 | 62,858 | 44,505 | 1.41 | NT | NT | NT | NT | NT | NT | NT | NT | 10.1 | 64,148 | 41,316 | 1.6 |
|  | 30 C. |  |  |  |  | NT | NT | NT | NT | NT | NT | NT | NT | NT | NT | NT | NT |
|  | 40 C. |  |  |  |  | 10.1 | 67,378 | 48,526 | NT | NT | NT | NT | NT | NT | NT | NT | NT |
| QBD 11 | 25 C. | 11.0 | 63,333 | 43,954 | 1.44 | NT | NT | NT | NT | NT | NT | NT | NT | 10.3 | 66,304 | 40,623 | 1.6 |
|  | 30 C. |  |  |  |  | NT | NT | NT | NT | NT | NT | NT | NT | NT | NT | NT | NT |
|  | 40 C. |  |  |  |  | 10.2 | 69,630 | 47,843 | NT | NT | NT | NT | NT | NT | NT | NT | NT |
| QBD 12* | 25 C. | 11.0 | 57,454 | 40,077 | 1.43 | NT | NT | NT | NT | NT | NT | NT | NT | 10.6 | 51,094 | 34,456 | 1.5 |
|  | 30 C. |  |  |  |  | 10.7 | 52,971 | 38,659 | 1.4 | 10.6 | 54,129 | 38,881 | 1.4 | NT | NT | NT | NT |
|  | 40 C. |  |  |  |  | 10.5 | 52,229 | 38,058 | 1.4 | 10.4 | 56,294 | 41,056 | 1.4 | NT | NT | NT | NT |
| QBD 13 | 25 C. | 11.0 | 67,902 | 47,260 | 1.44 | NT | NT | NT | NT | NT | NT | NT | NT | 10.1 | 82,146 | 49,203 | 1.7 |
|  | 30 C. |  |  |  |  | NT | NT | NT | NT | NT | NT | NT | NT | NT | NT | NT | NT |
|  | 40 C. |  |  |  |  | 10.1 | 76,040 | 52,316 | NT | NT | NT | NT | NT | NT | NT | NT | NT |
| QBD 14 | 25 C. | 11.0 | 57,467 | 39,979 | 1.44 | NT | NT | NT | NT | NT | NT | NT | NT | 10.7 | 50,707 | 34,082 | 1.5 |
|  | 30 C. |  |  |  |  | 10.8 | 52,750 | 38,385 | 1.4 | 10.8 | 54,683 | 39,302 | 1.4 | NT | NT | NT | NT |
|  | 40 C. |  |  |  |  | 10.8 | 53,096 | 38,548 | 1.4 | 10.6 | 60,617 | 43,580 | 1.4 | NT | NT | NT | NT |
| QBD 15 | 25 C. | 11.0 | 61,343 | 43,363 | 1.41 | NT | NT | NT | NT | NT | NT | NT | NT | 10.5 | 52,563 | 34,988 | 1.5 |
|  | 30 C. |  |  |  |  | NT | NT | NT | NT | 10.5 | 56,705 | 40,838 | 1.4 | NT | NT | NT | NT |
|  | 40 C. |  |  |  |  | 10.4 | 56,563 | 41,236 | 1.4 | NT | NT | NT | NT | NT | NT | NT | NT |
| QBD 16 | 25 C. | 11.0 | 53,768 | 36,688 | 1.47 | NT | NT | NT | NT | NT | NT | NT | NT | 10.7 | 52,713 | 34,718 | 1.5 |
|  | 30 C. |  |  |  |  | NT | NT | NT | NT | 10.7 | 56,643 | 40,372 | 1.4 | NT | NT | NT | NT |
|  | 40 C. |  |  |  |  | 10.7 | 61,535 | 43,249 | 1.4 | NT | NT | NT | NT | NT | NT | NT | NT |
| QBD 17 | 25 C. | 11.0 | 55,126 | 38,143 | 1.45 | NT | NT | NT | NT | NT | NT | NT | NT | 10.4 | 55,640 | 36,848 | 1.5 |
|  | 30 C. |  |  |  |  | NT | NT | NT | NT | 10.4 | 55,695 | 40,381 | 1.4 | NT | NT | NT | NT |
|  | 40 C. |  |  |  |  | 10.3 | 58,926 | 42,685 | 1.4 | NT | NT | NT | NT | NT | NT | NT | NT |

NT + not tested.

TABLE VIII

Stability Iron 2 mg/mL Compositions

| RTU 2 mg/mL ID | Temp | T0 pH | T0 Mw 34,000-60,000 | T0 Mn ≥24,000 | T0 PDI ≤1.7 | T=3M pH | T=3M Mw 34,000-60,000 | T=3M Mn ≥24,000 | T=3M PDI ≤1.7 | T=6M pH | T=6M Mw 34,000-60,000 | T=6M Mn ≥24,000 | T=6M PDI ≤1.7 | T=12M * P-50 Adjusted pH | Mw 34,000-60,000 | Mn ≥24,000 | PDI ≤1.7 |
|---|---|---|---|---|---|---|---|---|---|---|---|---|---|---|---|---|---|
| QBD 18 | 25 C. | 11.0 | 52,814 | 37,229 | 1.4 | 10.9 | 52,624 | 36,732 | 1.4 | 10.9 | 53,045 | 37,005 | 1.4 | 11.0 | 48,713 | 32,391 | 1.5 |
|  | 30 C. |  |  |  |  | 10.9 | 53,644 | 37,585 | 1.4 | 10.9 | 53,088 | 37,047 | 1.4 | NT | NT | NT | NT |
|  | 40 C. |  |  |  |  | 10.9 | 53,526 | 37,532 | 1.4 | 10.8 | 53,666 | 37,468 | 1.4 | NT | NT | NT | NT |
| QBD 18 HT | 25 C. | 10.9 | 52,585 | 37,071 | 1.4 | 10.9 | 53,482 | 37,401 | 1.4 | 10.8 | 52,834 | 36,768 | 1.4 | 10.9 | 49,727 | 33,025 | 1.5 |
|  | 30 C. |  |  |  |  | 10.9 | 53,412 | 37,358 | 1.4 | 10.8 | 52,886 | 36,891 | 1.4 | NT | NT | NT | NT |
|  | 40 C. |  |  |  |  | 10.8 | 53,444 | 37,383 | 1.4 | 10.7 | 53,720 | 37,460 | 1.4 | NT | NT | NT | NT |
| QBD 19* | 25 C. | 10.9 | 53,057 | 38,073 | 1.4 | 10.8 | 53,850 | 38,485 | 1.4 | 10.7 | 53,507 | 38,165 | 1.4 | 10.8 | 50,204 | 33,621 | 1.5 |
|  | 30 C. |  |  |  |  | 10.7 | 53,874 | 38,533 | 1.4 | 10.6 | 53,664 | 38,325 | 1.4 | NT | NT | NT | NT |
|  | 40 C. |  |  |  |  | 10.6 | 54,583 | 39,061 | 1.4 | 10.6 | 57,892 | 41,188 | 1.4 | NT | NT | NT | NT |

TABLE VIII-continued

Stability Iron 2 mg/mL Compositions

| RTU 2 mg/mL | | | T0 | | | | T = 3M | | | | T = 6M | | | | T = 12M * P-50 Adjusted | | |
|---|---|---|---|---|---|---|---|---|---|---|---|---|---|---|---|---|---|
| ID | Temp | pH | Mw 34,000-60,000 | Mn ≥24,000 | PDI ≤1.7 | pH | Mw 34,000-60,000 | Mn ≥24,000 | PDI ≤1.7 | pH | Mw 34,000-60,000 | Mn ≥24,000 | PDI ≤1.7 | pH | Mw 34,000-60,000 | Mn ≥24,000 | PDI ≤1.7 |
| QBD 20 | 25 C. | 10.9 | 52,810 | 37,147 | 1.4 | 10.9 | 53,515 | 37,430 | 1.4 | 10.9 | 52,844 | 36,782 | 1.4 | 10.9 | 49,696 | 33,005 | 1.5 |
|  | 30 C. |  |  |  |  | 10.9 | 53,422 | 37,432 | 1.4 | 10.8 | 52,715 | 36,688 | 1.4 | NT | NT | NT | NT |
|  | 40 C. |  |  |  |  | 10.8 | 53,315 | 37,589 | 1.4 | 10.7 | 53,520 | 37,324 | 1.4 | NT | NT | NT | NT |
| QBD 21 | 25 C. | 10.9 | 56,768 | 40,113 | 1.42 | 10.8 | 53,932 | 38,877 | 1.4 | 10.7 | 53,012 | 37,707 | 1.4 | 10.8 | 52,821 | 35,448 | 1.5 |
|  | 30 C. |  |  |  |  | 10.8 | 53,906 | 38,835 | 1.4 | 10.7 | 53,000 | 37,676 | 1.4 | NT | NT | NT | NT |
|  | 40 C. |  |  |  |  | 10.7 | 55,037 | 39,712 | 1.4 | 10.6 | 60,754 | 42,660 | 1.4 | NT | NT | NT | NT |

As shown in Tables VII and VIII all iron compositions had acceptable stability as indicated by the pH, Mw, Mn, and/or PDI over the 18 month time period when stored at 25° C., 30° C. and 40° C. at 60±5% RH. Iron compositions QBD 12 of Table VII and QBD 19 of Table VIII were selected as desirable as they had least amount of sodium and sucrose for sodium and sucrose restricted patients. These compositions had less excipients added and consistent pH, Mw, Mn, density, and/or PDI over the 18 month time period.

Example 7

Exemplary ready-to-use iron compositions are shown in Table IX below, which use the iron compositions QBD 12 of Table VII and QBD 19 of Table VIII.

TABLE IX

Compositions Ready-to-Use (RTU) (for Intravenous Infusion)

| Parameters | Description |
|---|---|
| Product Name | Venofer ® Ready-to-Use (RTU) (for Intravenous Infusion) |
| Strength | (per ml) 1 mg/mL and 2 mg/mL Iron |
| Presentations | 1 mg/mL |
|  | 100 mL Fill in a 100 mL Single-Dose Glass Vial |
|  | 2 mg/mL |
|  | 100 mL Fill in a 100 mL Single-Dose Glass Vial |
| Route of administration | Intravenous after dilution |
| Each mL contains: |  |
| 1 mg/mL | 1 mg |
| Iron as Iron Sucrose | 15 mg |
| Sucrose as Iron Sucrose | 80 mg |
| Sucrose, NF | 0.08 mg |
| Sodium Hydroxide, NF | Q.S. (density 1.037 g/mL) |
| Water for Injection, USP | 2 mg |
| 2 mg/mL**** | 30 mg |
| Iron as Iron Sucrose | 85 mg |
| Sucrose as Iron Sucrose | 0.96 mg |
| Sucrose, NF | Q.S. (density 1.047 g/mL) |
| Sodium Hydroxide, NF |  |
| Water for Injection, USP |  |
| *****HCl, NF may be used to adjust the pH as needed. | 15-25° C. |
| Storage Conditions of the Bulk Solution |  |
| Storage Conditions of the Finished Product | CRT (20-25° C.) |

Example 8

Exemplary compliance limits for the ready-to-use iron compositions of Example 7 are shown in Table X and Table XI below.

TABLE X

Quality Attributes for In-Process Testing and Corresponding Limits of Compliance—Iron Composition Ready-to-Use (RTU) 1 mg/mL

| Test | Limit of Compliance |
|---|---|
| Appearance | Brown aqueous solution |
| pH | 10.9-11.1 |
| Density (1.037 mg/mL) | 1.027-1.047 g/mL |
| Assay | 0.97-1.03 mg/mL (97.0-103.0%) |
| Bioburden | NMT 10 CFU/mL |

TABLE XI

Quality Attributes for In-Process Testing and
Corresponding Limits of Compliance—
Iron Composition- Ready-to-Use (RTU) 2 mg/mL

| Test | Limit of Compliance |
|---|---|
| Appearance | Brown aqueous solution |
| PH | 10.9-11.1 |
| Density (1.047 mg/mL) | 1.037-1.058 g/mL |
| Assay | 1.98-2.06 mg/mL (97.0-103.0%) |
| Bioburden | NMT 10 CFU/mL |

Tables X and XI show acceptable compliance limits for the iron compositions at 1 mg/mL and 2 mg/mL concentrations based on appearance, pH range, density range, and potency based on the label quantity. These iron compositions have little or no bacterial growth (acceptable bio burden) and are suitable for injection.

Example 9

The RTU iron compositions at 1 mg/mL and 2 mg/mL concentrations in Table XII can be prepared by adding the desired amount of sucrose to water for injection at 20° C.-25° C. in a tank and mixing the additives to form a mixture. To this mixture, sodium hydroxide is added and mixed. Iron is then added to the mixture while mixing and then 40% w/v sodium hydroxide, and/or hydrochloric acid is added to adjust the pH to the range of 10.9-11.1 to form the stable injectable iron composition. The injectable iron composition formed can then be filtered and/or autoclaved and placed in vial, bottle or bag and sealed.

TABLE XII

| Composition | Venofer® 20mg/mL Concentrated Inj. (each mL contains) | Venofer® IV Infusion in 0.9% Saline (each mL contains) | Venofer® IV RTU 1 mg/mL elemental iron (each mL contains) | Venofer® IV RTU 2 mg/mL elemental iron (each mL contains) |
|---|---|---|---|---|
| Iron-Sucrose Complex | 20 mg elemental iron | 1 mg elemental iron | 1 mg elemental iron | 2 mg elemental iron |
| Sucrose, NF | 300 mg | 15 mg | 95 mg (total sucrose)** | 115mg(total sucrose)** |
| NaOH, NF | N/A | N/A | 0.08 mg | 0.96 mg |
| NaCl, USP | N/A | 9 mg | N/A | N/A |
| NaOH, NF | pH adjusted to 10.9-11.1 | N/A | pH adjusted to 10.9-11.1 | pH adjusted to 10.9-11.1 |
| HCL, NF | N/A | N/A | N/A | pH adjusted to 10.9-11.1 |

**1 mg of iron is provided as an iron-sucrose complex containing a out 15 mg of sucrose, Total sucrose includes the amount of added sucrose and the amount already complexed with the elemental iron.

The RTU iron compositions at 1 mg/mL and 2 mg/mL concentrations in Table XII have about 3 times less sucrose than the Venofer® concentrated injection (20 mg/mL) but about 6-8 times more than the Venofer® IV infusion. The Venofer® IV infusion is diluted in sodium chloride, while the other compositions do not contain sodium chloride. RTU iron compositions at 1 mg/mL and 2 mg/mL concentrations have sodium (e.g., NaOH) and sucrose as stabilizing agents.

Example 10

The stability of the two RTU iron compositions of the current application (1 mg/mL iron and 2 mg/mL iron) from Table XII of Example 9 were compared to a) Venofer® 20 mg/mL, which is a concentrated commercially available formulation and b) Venofer® IV infusion, which is the concentrated Venofer® 20 mg/mL diluted in 0.9% sodium chloride to a concentration of 1 mg/mL for IV infusion. The compositions were assessed by monitoring parameters such as pH, Mw, Mn, PDI, appearance, and controlled release test for trivalent iron (T75). The stability results including the pH, Mw, Mn, PDI, appearance, and T75 are shown in Table XIII.

TABLE XIII

| | 40 ± 2° C./75 ± 5% RH (Accelerated ICH Stability) | | | | | | | | |
|---|---|---|---|---|---|---|---|---|---|
| Parameter (Specification) | pH (Proposed: 10.0-11.1) | | Mw (34,000-60,000 Da) | | Mn (NLT 24,000 Da) | | PDI (NMT 1.7) | | T75 (NMT 20 min) |
| Stability (Months) | T0 | T6M | T0 | T6M | T0 | T6M | T0 | T6M | T6M |
| Venofer® Inj., USP (20 mg/mL) | 10.9 | 10.7 | 50,761 | 58,315 | 35,427 | 38,975 | 1.4 | 1.5 | 11 |

TABLE XIII-continued

| | | 40 ± 2° C./75 ± 5% RH (Accelerated ICH Stability) | | | | | | | |
|---|---|---|---|---|---|---|---|---|---|
| Parameter (Specification) | pH (Proposed: 10.0-11.1) | | Mw (34,000-60,000 Da) | | Mn (NLT 24,000 Da) | | PDI (NMT 1.7) | | T75 (NMT 20 min) |
| Stability (Months) | T0 | T6M | T0 | T6M | T0 | T6M | T0 | T6M | T6M |
| [2]Venofer® IV Infusion in 0.9% NaCl (1 mg/mL) | 10.1 | **<10 @ T1M | 55,931 | **Precipitate | 38,907 | **Precipitate | 1.44 | >1.7 @ T1M | NT |
| [3]Venofer® RTU 1 mg/mL | 11.1 | 10.4 | 53,046 | 52,600 | 38,036 | 38,464 | 1.39 | 1.4 | 17 |
| [4]Venofer® RTU 2 mg/mL | 10.9 | 10.6 | 53,057 | 57,892 | 38,073 | 41,188 | 1.4 | 1.4 | NT |

NMT = Not More Than
NLT = Not Less Than
NT = Not Tested
[2]3RJ190618-5; [3]RJ191213-12 (F12)-Osmolality: 345 mOsm/kg;
[4]2DAB200807-1 (F19)-Osmolality: 480 mOsm/kg
RLD-Lot # 9353 has T75 = 12-14 minutes and pH 10.5-11.1

Table XIII shows acceptable compliance limits for the RTU iron compositions at 1 mg/mL and 2 mg/mL concentrations based on appearance, pH range, density range, and potency based on the label quantity at 6 months of storage even though the RTU iron compositions are at 1 mg/mL and 2 mg/mL concentrations. This is a significant improvement when compared to Venofer® IV infusion, which is the concentrated Venofer® 20 mg/mL diluted in 0.9% sodium chloride to a concentration of 1 mg/mL for IV infusion, which became unstable and unusable, as there was a precipitate that formed in about 1 month and the pH dropped to less than 10 after about 1 month of storage. The RTU iron compositions at 1 mg/mL and 2 mg/mL concentrations had no detectable precipitate formation.

Since modifications will be apparent to those of skill in the art, it is intended that this disclosure be limited only by the scope of the appended claims.

What is claimed is:

1. An injectable iron composition comprising water, an iron (III)-hydroxide-sucrose complex comprising 15 mg/mL to 30 mg/mL of sucrose complexed with iron (III)-hydroxide comprising 1 mg/mL to 2 mg/mL of elemental iron, the injectable iron composition having a total sucrose content of 57.5 mg/mL to 195 mg/mL, and a sodium compound in an amount of 0.07 mg/mL to 15 mg/mL of the injectable iron composition.

2. The injectable iron composition of claim 1, wherein the sodium compound is sodium hydroxide, and the injectable iron composition further comprises a buffering agent.

3. The injectable iron composition of claim 1, wherein the sodium compound comprises sodium hydroxide, and the injectable iron composition optionally comprises L-histidine.

4. The injectable iron composition of claim 1, wherein the injectable iron composition has a total volume of 1 mL to 250 mL or 250 mL to 500 mL.

5. The injectable iron composition of claim 2, wherein the injectable iron composition further comprises at least one of potassium hydroxide, calcium hydroxide or a combination thereof.

6. The injectable iron composition of claim 2, wherein the buffering agent is sodium carbonate, sodium bicarbonate, potassium carbonate, potassium bicarbonate, calcium carbonate, calcium bicarbonate or a mixture thereof.

7. The injectable iron composition of claim 2, wherein the buffering agent is L-histidine, glycine, arginine, tyrosine, lysine or a mixture thereof.

8. The injectable iron composition of claim 1, wherein the sodium compound is sodium hydroxide, sodium chloride, sodium gluconate or a combination thereof.

9. The injectable iron composition of claim 3, wherein the sodium hydroxide is in an amount from 0.08 mg/mL to 15 mg/mL and the L-histidine is in an amount from 0 mg/mL to 1.5 mg/ml of the injectable iron composition.

10. The injectable iron composition of claim 3, wherein the sodium hydroxide is in an amount from 0.07 mg/mL to 0.97 mg/mL, and the L-histidine is in an amount from 0 mg/mL to 1.5 mg/ml of the injectable iron composition.

11. The injectable iron composition of claim 1, wherein the injectable iron composition further comprises L-histidine.

12. The injectable iron composition of claim 1, wherein the iron (III)-hydroxide-sucrose complex comprises 15 mg/mL to 30 mg/mL of sucrose bound to 1 mg/mL to 2 mg/mL of the elemental iron and the injectable iron composition comprises an unbound sucrose in an amount of 42.5 mg/mL to 165 mg/mL so that the injectable iron composition has the total sucrose content of 57.5 mg/mL to 195 mg/mL of the injectable iron composition.

13. The injectable iron composition of claim 1, wherein the injectable iron composition has a pH from 9.6 to 11.4.

14. The injectable iron composition of claim 1, wherein (i) a weight average molecular weight (Mw) of the iron (III)-hydroxide-sucrose complex is 34,000 Daltons to 60,000 Daltons; (ii) a number average molecular weight (Mn) of the iron (III)-hydroxide-sucrose complex is 24,000 Daltons to 60,000 Daltons; (iii) a polydispersity index of the iron (III)-hydroxide-sucrose complex is 1.0 to 1.7; and (iv) the injectable iron composition maintains a density of 1.027 to 1.047 g/mL or 1.037 to 1.058 g/mL for a period of up to 24 months.

15. The injectable iron composition of claim 1, wherein the injectable iron composition comprises 1 mg of elemental iron per 1 mL of the injectable iron composition; 95 mg of a total sucrose content per 1 mL of the injectable iron composition; and the sodium compound comprises 0.08 mg of sodium hydroxide per 1 mL of the injectable iron composition.

16. The injectable iron composition of claim 1, wherein the injectable iron composition comprises 2 mg of elemental iron per 1 mL of the injectable iron composition; 115 mg of a total sucrose content per 1 mL of the injectable iron composition; and the sodium compound comprises 0.96 mg of sodium hydroxide per 1 mL of the injectable iron composition.

17. The injectable iron composition of claim 1, wherein the iron (III)-hydroxide-sucrose complex comprises a polynuclear iron (III)-hydroxide-sucrose complex having a weight average molecular weight of 34,000 to 60,000 Daltons.

18. The injectable iron composition of claim 15, wherein the iron (III)-hydroxide-sucrose complex comprises a polynuclear iron (III)-hydroxide-sucrose complex having a weight average molecular weight of 34,000 to 60,000 Daltons.

19. The injectable iron composition of claim 16, wherein the iron (III)-hydroxide-sucrose complex comprises a polynuclear iron (III)-hydroxide-sucrose complex having a weight average molecular weight of 34,000 to 60,000 Daltons.

20. The injectable iron composition of claim 1, wherein the injectable iron composition is useful for treating a human patient.

21. The injectable iron composition of claim 1, wherein the injectable iron composition is useful for treating iron deficiency anemia in a human patient with chronic kidney disease.

22. The injectable iron composition of claim 15, wherein the injectable iron composition is useful for treating a human patient.

23. The injectable iron composition of claim 15, wherein the injectable iron composition is useful for treating iron deficiency anemia in a human patient with chronic kidney disease.

24. The injectable iron composition of claim 16, wherein the injectable iron composition is useful for treating a human patient.

25. The injectable iron composition of claim 16, wherein the injectable iron composition is useful for treating iron deficiency anemia in a human patient with chronic kidney disease.

26. The injectable iron composition of claim 15, wherein the injectable iron composition has a weight average molecular weight (Mw) of 34,000 Daltons to 60,000 Daltons; a number average molecular weight (Mn) of 24,000 Daltons to 60,000 Daltons; a polydispersity index of 1.0 to 1.7; and the injectable iron composition maintains a density of 1.027 to 1.047 g/mL or 1.037 to 1.058 g/mL for a period of up to 24 months.

27. The injectable iron composition of claim 16, wherein the injectable iron composition has a weight average molecular weight (Mw) of 34,000 Daltons to 60,000 Daltons; a number average molecular weight (Mn) of 24,000 Daltons to 60,000 Daltons; a polydispersity index of 1.0 to 1.7; and the injectable iron composition maintains a density of 1.027 to 1.047 g/mL or 1.037 to 1.058 g/mL for a period of up to 24 months.

28. The injectable iron composition of claim 15, wherein the injectable iron composition has a volume of 100 mL or 200 mL.

29. The injectable iron composition of claim 16, wherein the injectable iron composition has a volume of 100 mL.

30. An injectable iron sucrose composition comprising an iron (III)-hydroxide-sucrose complex comprising 15 mg/mL to 30 mg/mL of sucrose complexed with iron (III)-hydroxide comprising 1 mg/mL to 2 mg/mL of elemental iron, the injectable iron sucrose composition having a total sucrose content of 57.5 mg/mL to 195 mg/mL, a sodium compound in an amount of 0.07 mg/mL to 15 mg/mL, and optionally L-histidine from 0 mg/mL to 1.5 mg/mL of the injectable iron sucrose composition.

31. The injectable iron sucrose composition of claim 30, wherein the iron (III)-hydroxide-sucrose complex comprises a polynuclear iron (III)-hydroxide-sucrose complex in colloidal form.

32. The injectable iron sucrose composition of claim 30, wherein the iron sucrose composition is in colloidal form and comprises water.

33. The injectable iron sucrose composition of claim 30, wherein the injectable iron sucrose composition comprises 1 mg of elemental iron per 1 mL of the injectable iron sucrose composition; 95 mg of a total sucrose content per 1 mL of the injectable iron sucrose composition; and the sodium compound comprises 0.08 mg of sodium hydroxide per 1 mL of the injectable iron sucrose composition.

34. The injectable iron sucrose composition of claim 30, wherein the injectable iron sucrose composition comprises 2 mg of elemental iron per 1 mL of the injectable iron sucrose composition; 115 mg of a total sucrose content per 1 mL of the injectable iron sucrose composition; and the sodium compound comprises 0.96 mg of sodium hydroxide per 1 mL of the injectable iron sucrose composition.

\* \* \* \* \*